US009623178B2

(12) United States Patent
Krebs et al.

(10) Patent No.: US 9,623,178 B2
(45) Date of Patent: Apr. 18, 2017

(54) DEPLOYABLE JOINT INFECTION TREATMENT SYSTEM

(71) Applicant: THE CLEVELAND CLINIC FOUNDATION, Cleveland, OH (US)

(72) Inventors: Viktor E. Krebs, Rocky River, OH (US); Wael K. Barsoum, Bay Village, OH (US); Bret E. Hartzell, Massillon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 551 days.

(21) Appl. No.: 14/151,025

(22) Filed: Jan. 9, 2014

(65) Prior Publication Data

US 2014/0194810 A1 Jul. 10, 2014

Related U.S. Application Data

(60) Provisional application No. 61/750,936, filed on Jan. 10, 2013.

(51) Int. Cl.
*A61M 1/00* (2006.01)
*A61M 5/172* (2006.01)
*A61B 17/34* (2006.01)

(52) U.S. Cl.
CPC ......... *A61M 5/172* (2013.01); *A61B 17/3421* (2013.01); *A61M 1/0039* (2013.01); *A61M 1/0084* (2013.01); *A61B 2217/005* (2013.01)

(58) Field of Classification Search
CPC .......... A61B 2217/005; A61B 17/3421; A61B 17/1219; A61B 17/88; A61B 2217/007;

(Continued)

(56) References Cited

U.S. PATENT DOCUMENTS 4,650,462 A * 3/1987 DeSatnick ............... A61B 1/12
    601/2
5,616,121 A * 4/1997 McKay ............... A61M 1/0062
    604/28

(Continued)

FOREIGN PATENT DOCUMENTS

WO 2010075565 A2 7/2010
WO 2011038949 A1 4/2011

OTHER PUBLICATIONS

International Search Report and Written Opinion for PCT/US2014/010800, mailed May 23, 2014, pp. 1-18.

*Primary Examiner* — Nathan R Price
*Assistant Examiner* — Gerald Landry, II
(74) *Attorney, Agent, or Firm* — Tarolli, Sundheim, Covell & Tummino LLP

(57) ABSTRACT

A deployable infection treatment system includes a cannula device comprising a cannula body having a proximal end, a flared distal end, and a lumen extending therebetween. The lumen has a longitudinal x-axis extending therethrough. A sponge or drain is provided, the sponge having a distal end and a proximal end, wherein in a non-deployed configuration, the sponge is compressed within the cannula body's lumen and in a deployed configuration the distal end of the sponge expands out of the cannula body's lumen. An integrated pump and vacuum device is provided, wherein when the sponge is in a deployed configuration, the device is in fluid communication with a therapeutic fluid source. The pump controls the delivery of the therapeutic fluid to the proximal end of the sponge. The vacuum controls the extraction of the therapeutic fluid and infectious material from the proximal end of the sponge.

15 Claims, 21 Drawing Sheets

(58) Field of Classification Search
CPC .... A61M 5/172; A61M 1/0039; A61M 27/00; A61M 1/0084; A61M 1/0023; A61M 1/0058; A61M 29/02
USPC .... 604/27, 35, 104, 131, 313, 514, 540, 543
See application file for complete search history.

(56) References Cited

U.S. PATENT DOCUMENTS

| | | | | |
|---|---|---|---|---|
| 5,827,224 | A * | 10/1998 | Shippert | A61B 17/12022 |
| | | | | 604/104 |
| 6,569,839 | B1 * | 5/2003 | McKay | A61M 1/0005 |
| | | | | 514/169 |
| 2002/0198550 | A1 | 12/2002 | Nash et al. | |
| 2007/0060913 | A1 * | 3/2007 | Kucklick | A61B 1/015 |
| | | | | 604/541 |
| 2007/0173754 | A1 * | 7/2007 | Kucklick | A61B 17/3421 |
| | | | | 604/19 |
| 2007/0185380 | A1 * | 8/2007 | Kucklick | A61B 1/00135 |
| | | | | 600/114 |
| 2007/0219497 | A1 * | 9/2007 | Johnson | A61M 1/0092 |
| | | | | 604/131 |
| 2009/0005757 | A1 * | 1/2009 | Taber | A61M 25/0082 |
| | | | | 604/523 |
| 2009/0187259 | A1 * | 7/2009 | Argenta | A61M 1/0023 |
| | | | | 623/23.74 |
| 2010/0217401 | A1 | 8/2010 | de Beaubien | |
| 2011/0040279 | A1 * | 2/2011 | Walsh | A61L 27/3834 |
| | | | | 604/506 |
| 2011/0264073 | A1 * | 10/2011 | Cragg | A61B 17/12195 |
| | | | | 604/508 |
| 2013/0023840 | A1 * | 1/2013 | Loske | A61M 1/0084 |
| | | | | 604/319 |
| 2013/0237908 | A1 * | 9/2013 | Clark | A61B 17/12181 |
| | | | | 604/96.01 |

\* cited by examiner

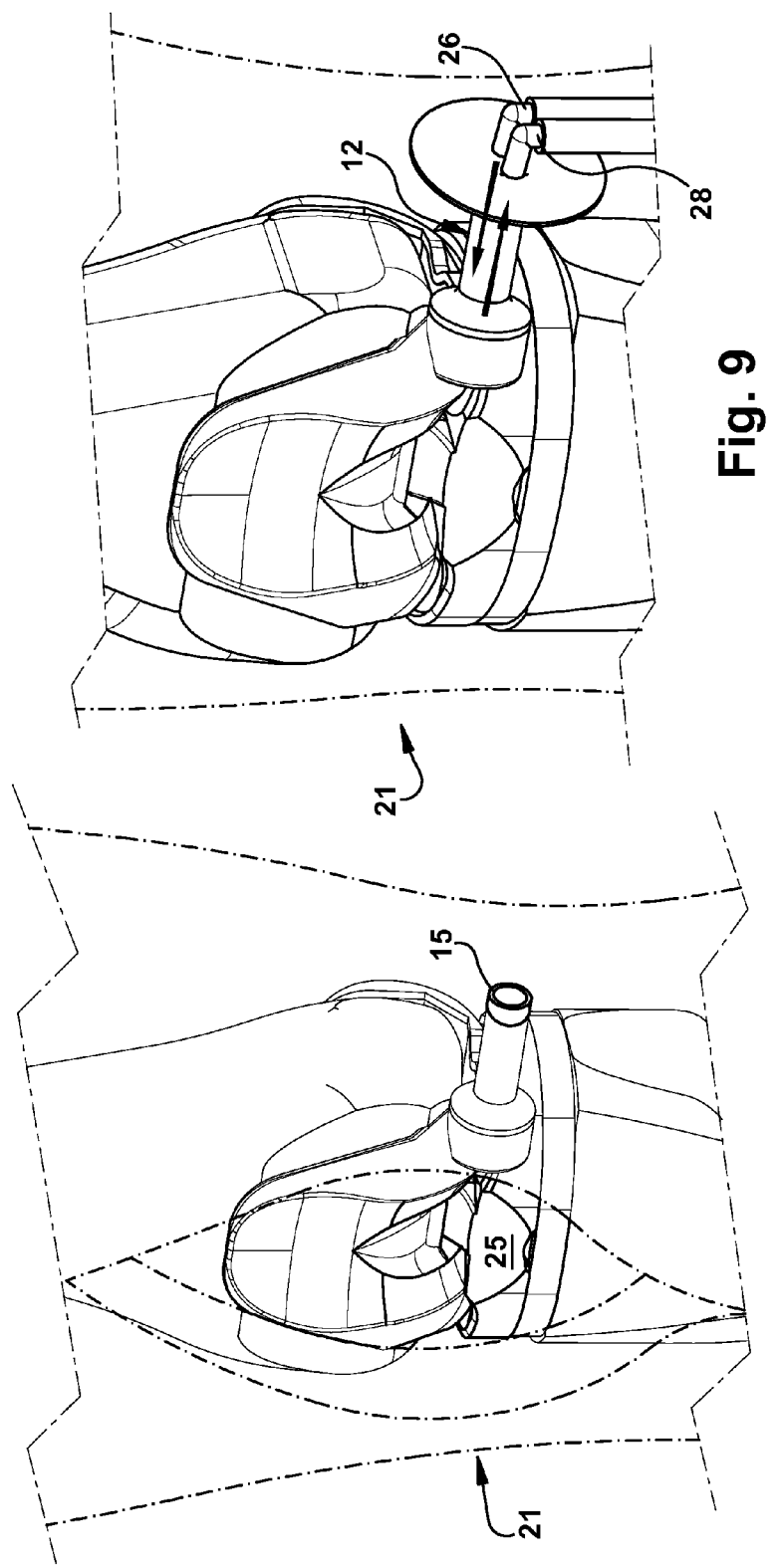

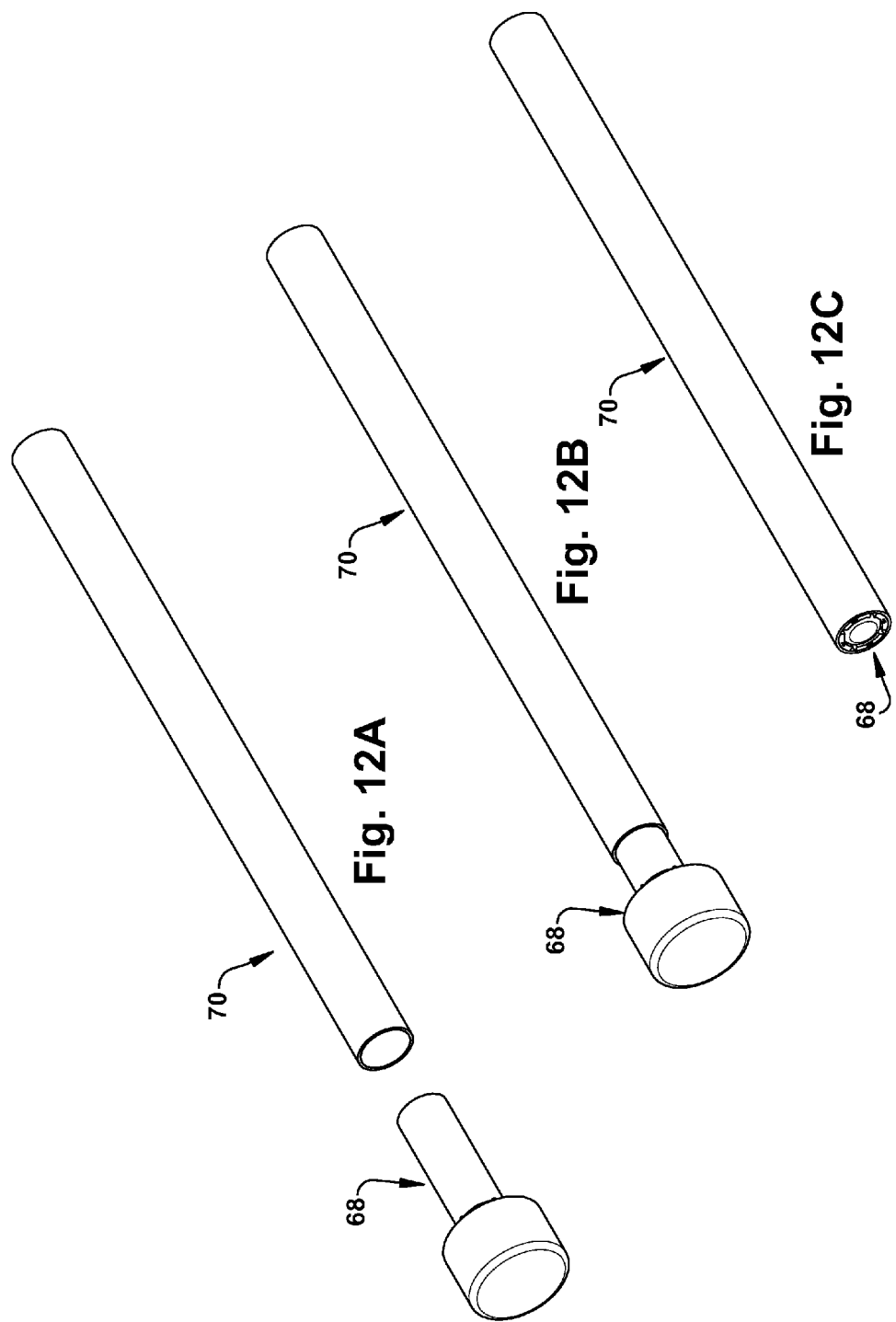

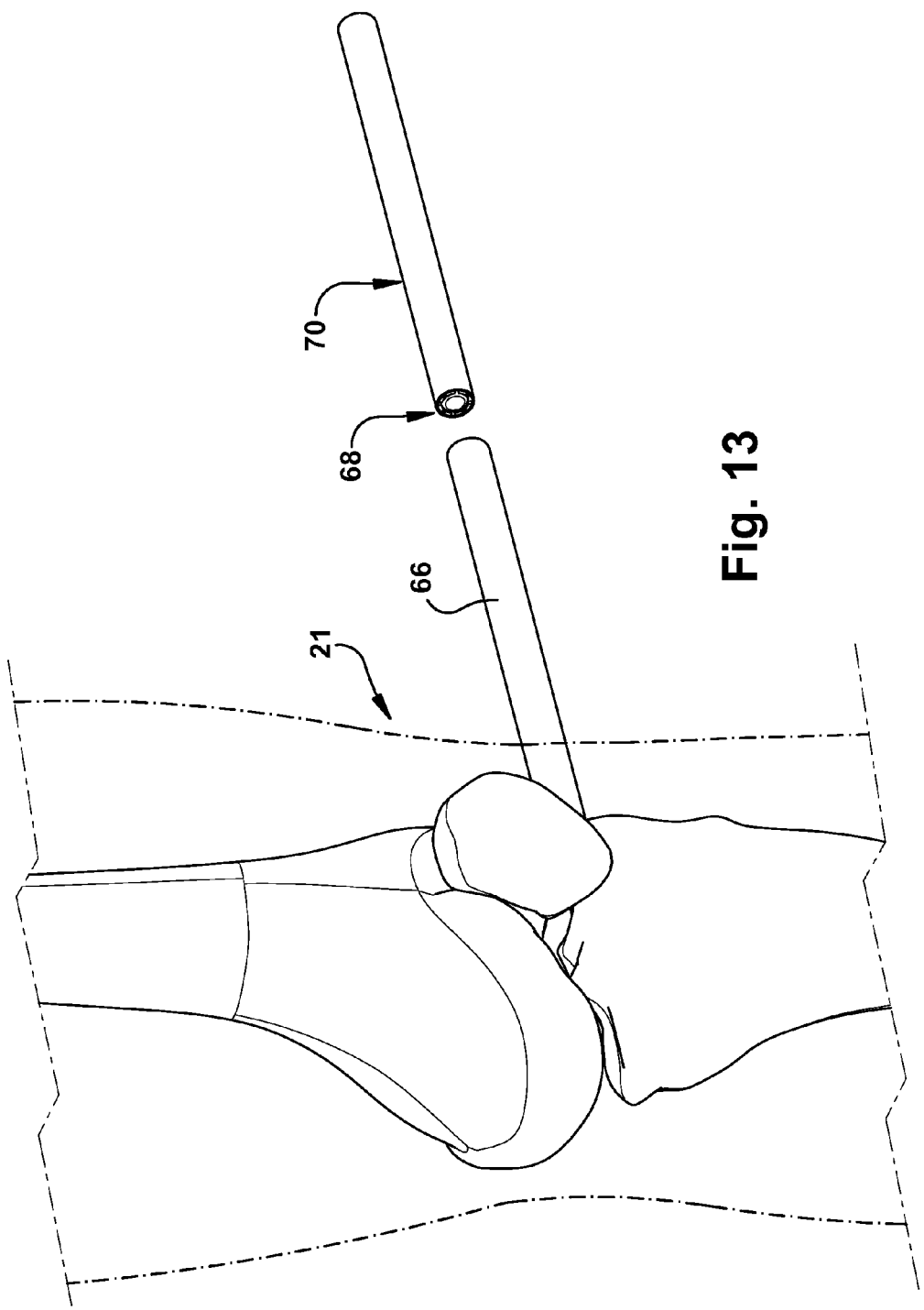

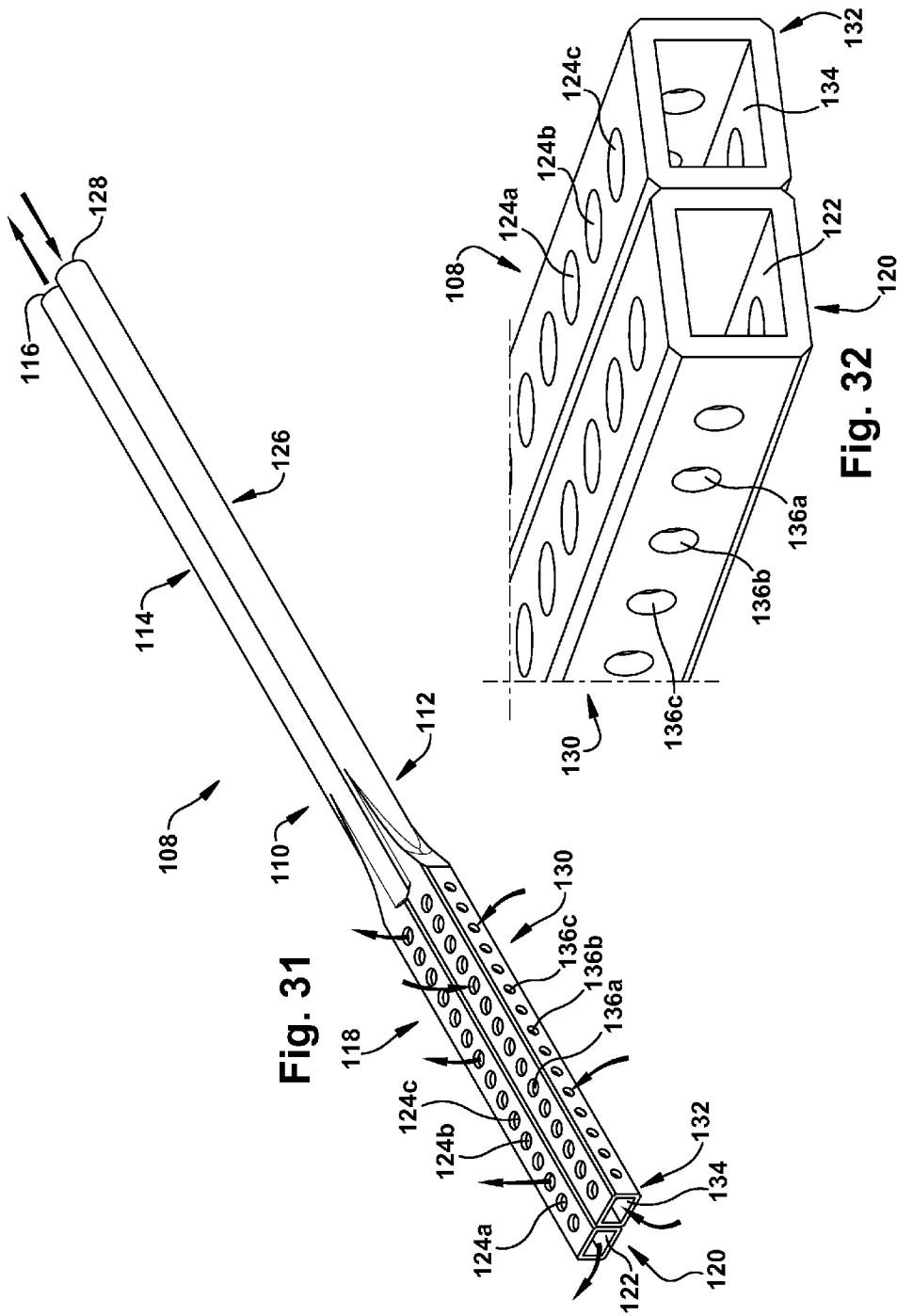

DEPLOYABLE JOINT INFECTION TREATMENT SYSTEM

RELATED APPLICATION

This application claims priority from U.S. Provisional Application No. 61/750,936, filed 10 Jan. 2013, the subject matter of which is incorporated herein by reference in its entirety.

TECHNICAL FIELD

The present invention relates to systems and methods for treating joint infections.

BACKGROUND

A joint infection can cause a severe and potentially destructive form of arthritis, often referred to as septic arthritis. Bacterial joint infections can be caused by a number of different organisms and can occur in both natural and artificial joints (i.e., after a knee replacement). The bacteria can enter the joint by traveling through the blood or by direct entrance into the joint from trauma or from surgery. Previous joint surgery and a depressed immune system increase the risk of the disorder.

In most cases, antibiotics are given following a surgical debridement and lavage. Drainage of the joint fluid may require repeated needle aspiration or, for some deep joints (i.e., hip, shoulder), surgical placement of a drainage tube.

As mentioned above, patients who have artificial joints are at a greater risk of developing a joint infection. Approximately 0.5 to 1 percent of patients with replacement joints will develop such an infection after surgery. Infections can occur early in the course of recovery from joint replacement surgery (within the first two months) or much later. Unfortunately, artificial joint infections may be difficult to treat. This is due, at least in part, to the development of a biofilm within the joint. A biofilm develops when bacteria adhere to the solid surface of the artificial joint. Biofilm makes it difficult for the bacteria to be identified and destroyed by the body's defenses or by antibiotic medications. Treatment of artificial joint infections can also involve surgery to remove infected tissue. In many cases, the artificial joint must be removed, at least temporarily. After a period of antibiotic treatment and once the infection is controlled, a new prosthesis may be placed. However, in some cases, it is not possible to replace the prosthetic joint, and surgery to fuse the bones or amputate the extremity is recommended instead.

SUMMARY

In an embodiment of the present invention, a deployable infection treatment system is described. A cannula device comprises a cannula body having a proximal end, a flared distal end, and a lumen extending therebetween. The lumen has a longitudinal x-axis extending therethrough. A sponge or drain is provided, the sponge having a distal end and a proximal end, wherein in a non-deployed configuration, the sponge is compressed within the cannula body's lumen and in a deployed configuration the distal end of the sponge expands out of the cannula body's lumen. An integrated pump and vacuum device is provided, wherein when the sponge is in a deployed configuration, the device is in fluid communication with a therapeutic fluid source. The pump controls the delivery of the therapeutic fluid to the proximal end of the sponge. The vacuum controls the extraction of the therapeutic fluid and infectious material from the proximal end of the sponge.

In an embodiment of the present invention, a deployable infection treatment system is described. A cannula device comprises a cannula body having a proximal end, a flared distal end, and a lumen extending therebetween. The lumen has a longitudinal x-axis extending therethrough. A sponge has a distal end and a proximal end, wherein in a non-deployed configuration, the sponge is compressed within the cannula body's lumen and in a deployed configuration the distal end of the sponge expands out of the cannula body's lumen. A retrieval cable extends longitudinally through the sponge and is attached to a fastener at the distal end of the sponge.

In an embodiment of the present invention, a deployable infection treatment system is described. A cannula device comprises a cannula body having a proximal end, a flared distal end, and a lumen extending therebetween. The lumen has a longitudinal x-axis extending therethrough. A sponge has a distal end and a proximal end, wherein in a non-deployed configuration, the sponge is compressed within the cannula body's lumen and in a deployed configuration the distal end of the sponge expands out of the cannula body's lumen. A rollable sheath is disposed on the distal end of the sponge. The rollable sheath comprises a sleeve and axially extending retrieval cords attached to the sleeve and axially extending through the cannula body.

In an embodiment of the present invention, a deployable infection treatment system is described. A cannula device comprises a cannula body having a proximal end, a flared distal end, and a lumen extending therebetween. The lumen has a longitudinal x-axis extending therethrough. The flared distal end comprises a plurality of elastic strips disposed longitudinally about the flared distal end. A sponge has a distal end and a proximal end, wherein in a non-deployed configuration, the sponge is compressed within the cannula body's lumen and in a deployed configuration the distal end of the sponge expands out of the cannula body's lumen. A plurality of axially extending retrieval cables are provided. Each one of the retrieval cables is attached to a respective one of the elastic strips.

In an embodiment of the present invention, a deployable infection treatment system is described. A cannula comprises an outflow section comprising a proximal portion having a proximal open end, a distal portion having a closed distal end, and an outflow channel extending between the proximal end and distal end. The distal portion comprises a plurality of outlets in fluid communication with the outflow channel. An inflow section comprises a proximal portion having a proximal open end, a distal portion having a closed distal end, and an outflow channel extending between the proximal end and the distal end. The distal portion comprises a plurality of inlets in fluid communication with the inflow channel, wherein in a deployed configuration the distal portions of the outflow and inflow sections mutually form a loop-like shape. An integrated pump and vacuum device is provided, wherein when the cannula is in a deployed configuration, the device is in fluid communication with a therapeutic fluid source. The pump controls the delivery of the therapeutic fluid to the outflow channel. The vacuum controls the extraction of the therapeutic fluid and infectious materials from the inflow channel.

In an embodiment of the present invention, a deployable infection treatment system is described. A cannula comprises an outflow section comprising a proximal portion having an open proximal end, a distal portion having an open distal end, and an outflow channel extending between the proximal end and the distal end. The distal portion comprises a plurality of outlets in fluid communication with the outflow channel. An inflow section comprises a proximal portion having an open proximal end, a distal portion having an open distal end, and an inflow channel extending between the proximal end and the distal end. The distal portion comprises a plurality of inlets in fluid communication with the inflow channel, wherein each of the distal portions of the outflow section and the inflow section have a substantially rectangular cross-sectional shape. An integrated pump and vacuum device is provided, wherein when the cannula is in a deployed configuration, the device is in fluid communication with a therapeutic fluid source. The pump controls the delivery of the therapeutic fluid to the outflow channel. The vacuum controls the extraction of the therapeutic fluid and infectious materials from the inflow channel.

In an embodiment of the present invention, a deployable infection treatment system is described. A cannula comprises a proximal portion with an open proximal end, a helically shaped distal portion with a closed distal end, and a channel extending between the proximal end and the distal end. The distal portion comprises a plurality of ports that are in fluid communication with the channel.

BRIEF DESCRIPTION OF THE DRAWINGS

For a better understanding of the invention, reference may be made to the accompanying drawings, in which:

FIGS. 3-9 schematically depict a sequence of operation of the embodiment of FIG. 1 in an example use environment;

FIGS. 10-16 schematically depict a sequence of operation of the embodiment of FIG. 1 in another example use environment;

FIG. 31 is a perspective side view of an embodiment of the present invention;

FIG. 32 is a partial front view of the embodiment of FIG. 31;

DETAILED DESCRIPTION

The present invention is directed to systems and methods for treating joint infections in a patient. The patient may be a mammal, such as a human being. Such infections can occur in a virgin joint and/or in a joint space after implantation of a medical device, such as a prosthesis. Regarding the latter, systems and methods of the present invention may be employed as part of a revision surgery to treat the infection site after removal of an existing medical device and prior to implantation of a new medical device in the joint space. Systems and methods can also or instead be used an initial treatment of an infected joint with an existing implant upon discovering the infection but prior to replacement of the implant. Embodiments of the present invention allow a therapeutic fluid, such as an antibiotic, to be introduced into the joint space and allow the therapeutic fluid and infectious materials to be extracted from the joint space. Although the present invention will be described with respect to a knee joint infection, the present invention can also be employed to treat other types of joint infections such as, for example, hip, shoulder, and elbow infections, as well as patient infections which are not located in a joint area.

Figure 1:
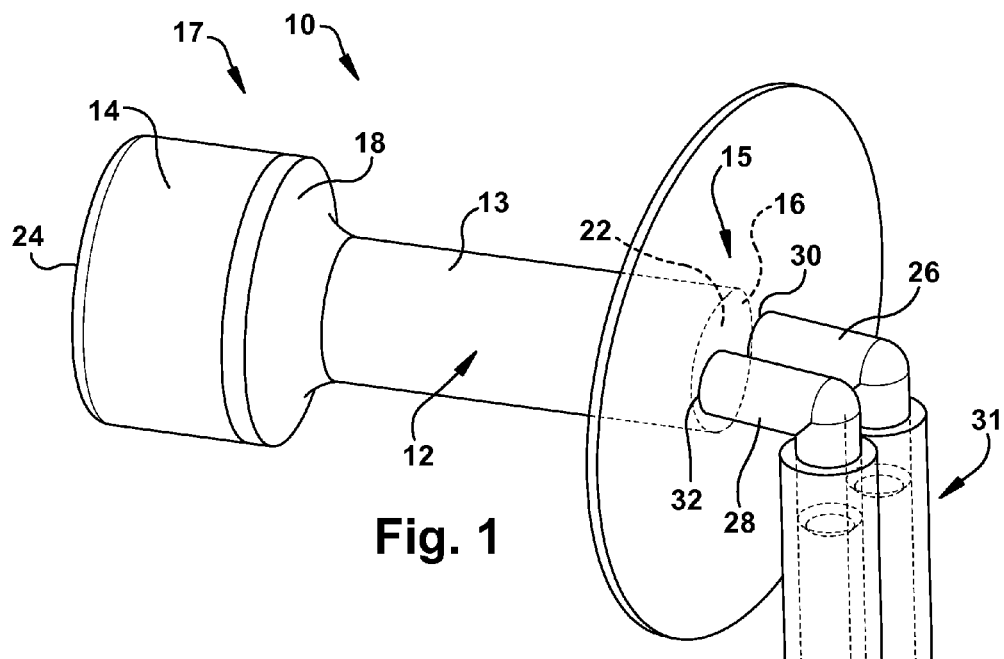
FIG. 1 is a partial side perspective view of an embodiment of the present invention.
Figure 2:
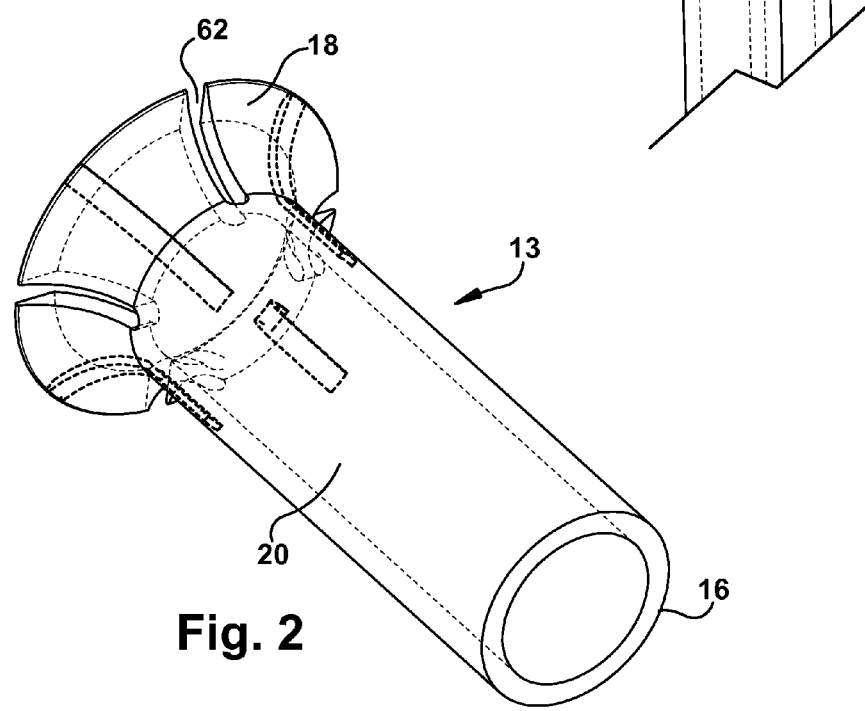
FIG. 2 is a partial top perspective view of the embodiment of FIG. 1.

Referring to FIGS. 1 and 2, an embodiment of the present invention provides a deployable infection treatment system 10 comprising a cannula device 12 and an integrated pump and vacuum device 31. Cannula device 12 has a proximal end 15 and a distal end 17. Cannula device 12 comprises a cannula body 13 and a sponge 14 or a drain. Cannula body 13 comprises a proximal end 16, a flared distal end 18, and a lumen 20 extending therebetween. Lumen 20 has a longitudinal x-axis extending therethrough. Sponge 14 has a proximal end 22 and a distal end 24. In a non-deployed configuration, distal end 24 of sponge 14 is compressed within lumen 20. In a deployed configuration, as shown in FIG. 1, distal end 24 expands out of lumen 20 at distal end 18 of cannula body 13. The integrated pump and vacuum device 31 is in fluid communication with sponge 14. The integrated pump and vacuum device is also in fluid communication with a therapeutic fluid source, such as an antibiotic or other medication to treat infections. During use, the pump controls the delivery of the therapeutic fluid to the proximal end 22 of sponge 14. The vacuum controls the extraction of the therapeutic fluid and infectious materials from proximal end 22 of sponge 14.

The integrated pump and vacuum device can comprise a first tube 26 and a second tube 28. Each of first and second tubes 26 and 28 has a respective proximal end (not shown) and a respective distal end 30 and 32. Distal end 30 of first tube 26 is in fluid communication with proximal end 22 of sponge 14 and the proximal end of first tube 26 is in fluid communication with a pump. The pump, in turn, is in fluid communication with a therapeutic fluid source. Distal end 32 of second tube 28 is in fluid communication with proximal end 22 of sponge 14 and the proximal end of second tube 28 is in fluid communication with a vacuum. In the embodiment shown in FIG. 1, tubes 26 and 28 are shown in direct contact or abutment with sponge 14 but the tubes could also be indirectly in contact with sponge 14 so long as the tubes perform their intended function.

Figure 4:
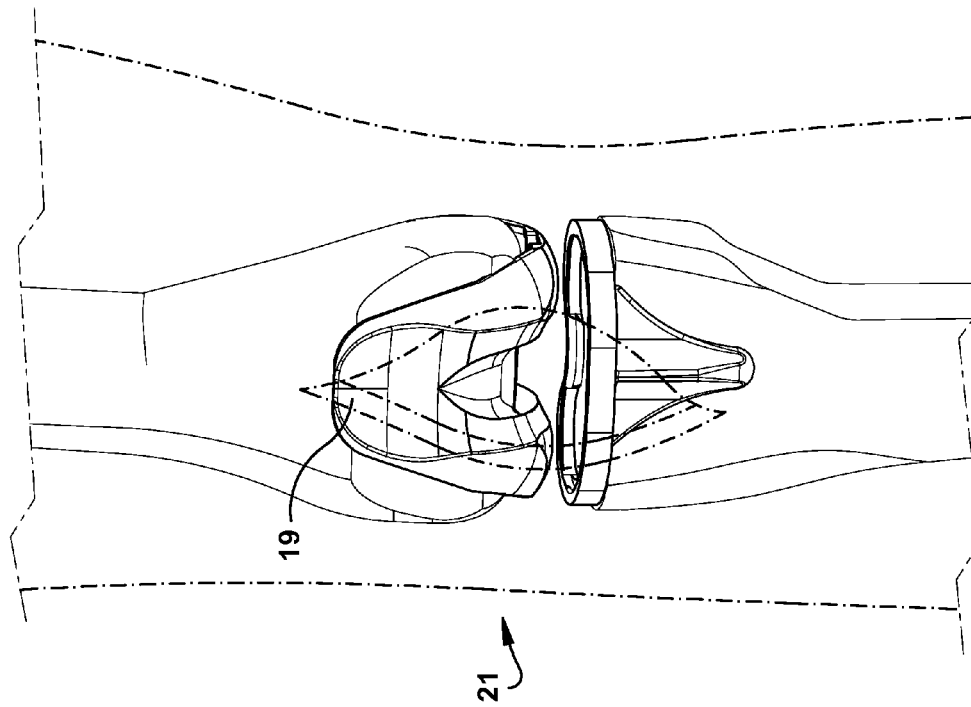
Figure 3:
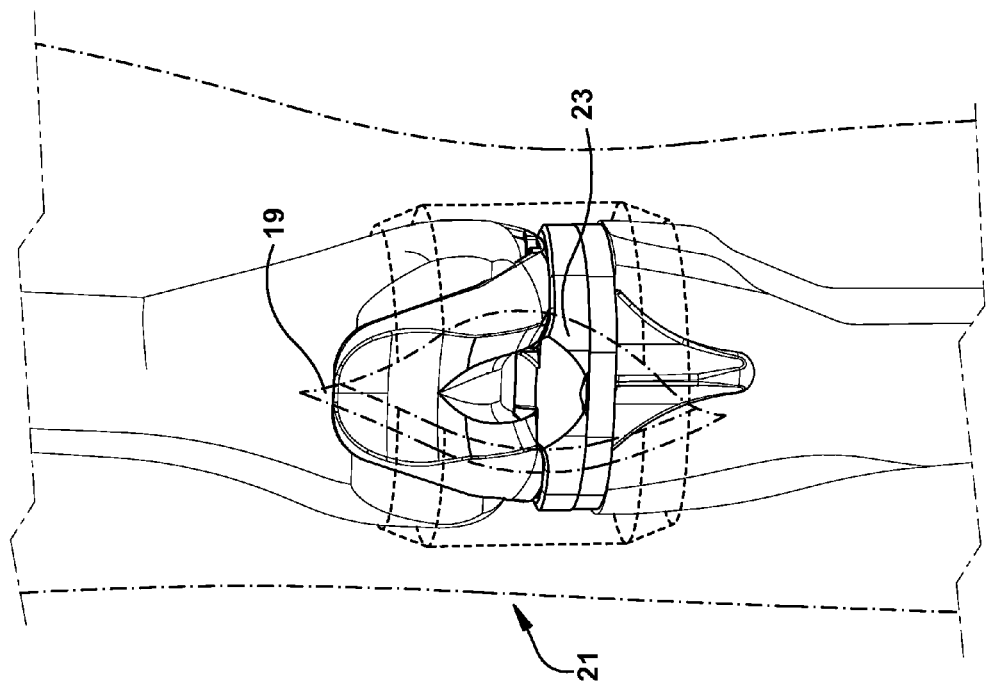
Figure 5:
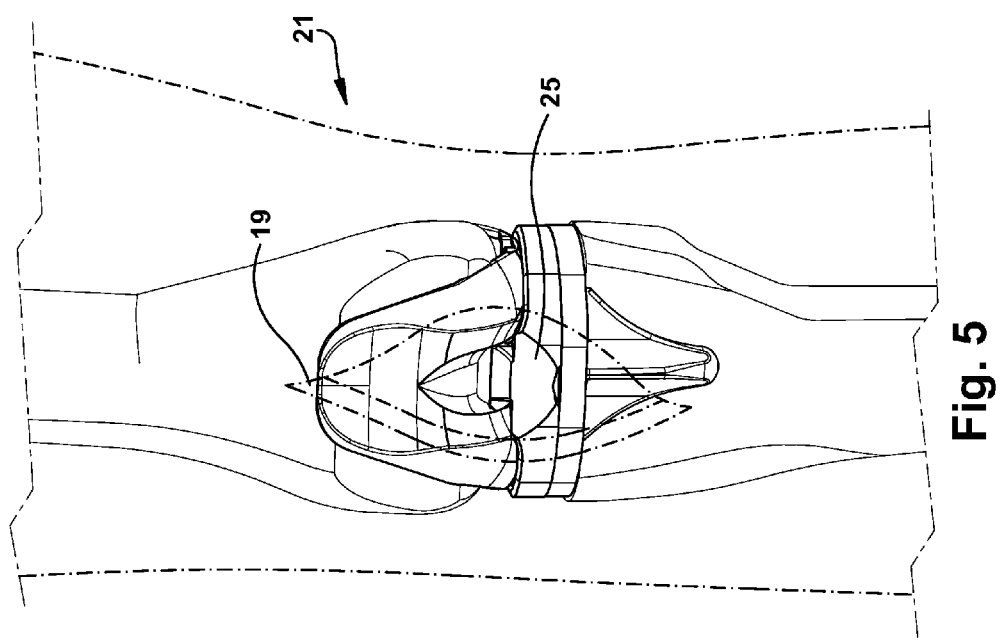
Figure 6:
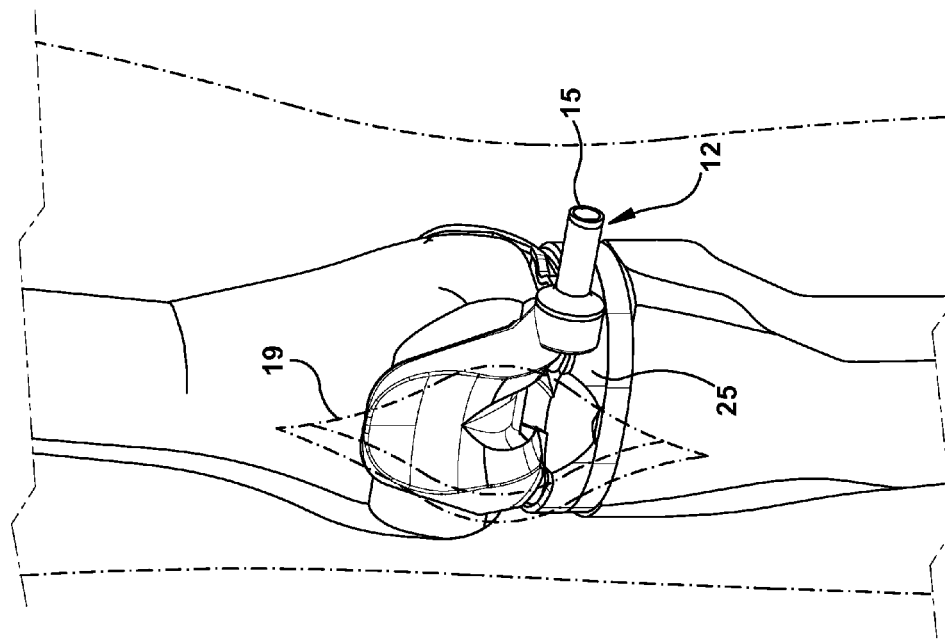
Figure 7:
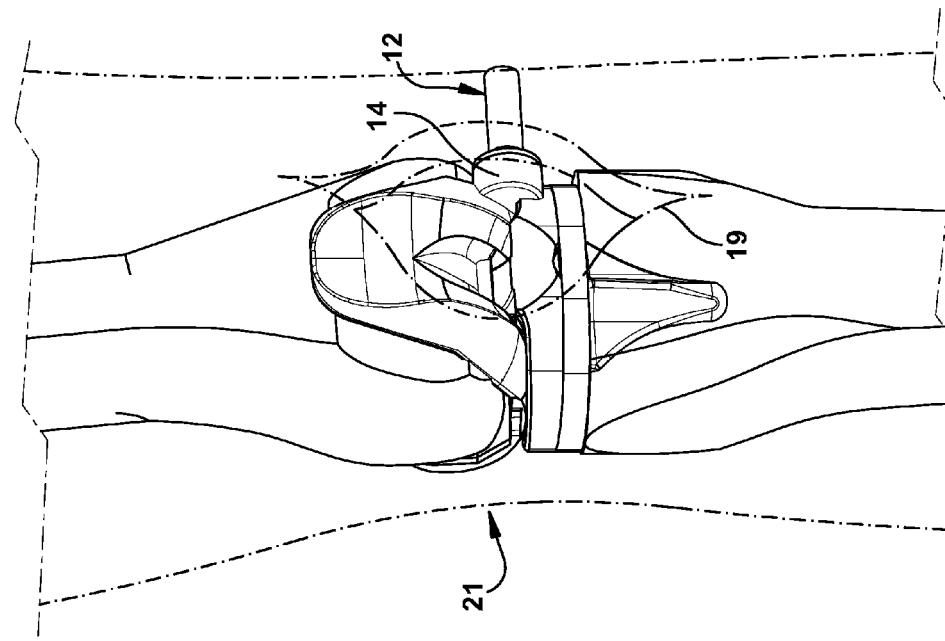

The present invention also provides methods of using an infection treatment system. For example, the above-described system can be used to treat an infected knee joint that has an existing implant or to treat an infection of a virgin joint. The below example steps will be described with respect to the former and with reference to FIGS. 3 to 9. Example steps of a method include making an incision 19 in the patient's knee 21 to expose the knee joint as shown in FIG. 3. All or a portion of the existing implant can be removed, such as the polytibial component 23, as shown in FIG. 4. The knee joint can then be irrigated to flush out contaminants. The removed implant portion can then be replaced with a new implant portion 25 as shown in FIG. 5. An opening can be created from inside the joint capsule to outside the patient's skin as shown in FIGS. 6 and 7. Cannula device 12 can then be inserted into the opening as seen in FIGS. 6 and 7. To expose sponge 14, cannula body 13 can be axially retracted to expose distal end 24 of sponge 14 housed in cannula body's lumen 20. Thus, upon axial retraction of cannula body 13, the sponge 14 is no longer compressed within cannula body 20 (i.e., is no longer in a non-deployed configuration) and assumes an expanded configuration (i.e., a deployed configuration) as seen in FIG. 6. Cannula body 13 can comprise a flexible polymer such as, for example, silicone or nylon. Distal end 24 of sponge 14 can have a diameter greater than flared distal end 18 of cannula body 13 in a deployed configuration of sponge 14. Referring to FIG. 8, the joint can then be closed. As seen in FIG. 8, proximal end 15 of cannula 12 is exposed outside the patient's body. Flared distal end 18 of cannula body 13 prevents cannula device 12 from inadvertently being pulled out of the patient's body during treatment.

An integrated pump and vacuum device can be positioned against the exposed proximal end 22 of sponge 14 to irrigate the joint space. As seen in FIG. 9, in certain embodiments, the integrated pump and vacuum device comprises first tube 26 and second tube 28 as described above. A treatment solution can be delivered to sponge 14 through first tube 26. Such a solution travels through the porous structure of sponge 14 and effluxes distal end 24 of sponge 14 into the joint space. The therapeutic fluid and infectious materials can be suctioned out of the joint space and exit the patient's body through second tube 28. This infusion and extraction steps can be cyclically alternated and the cycles can be repeated as many times as necessary to flush out the infected joint.

Figure 11:
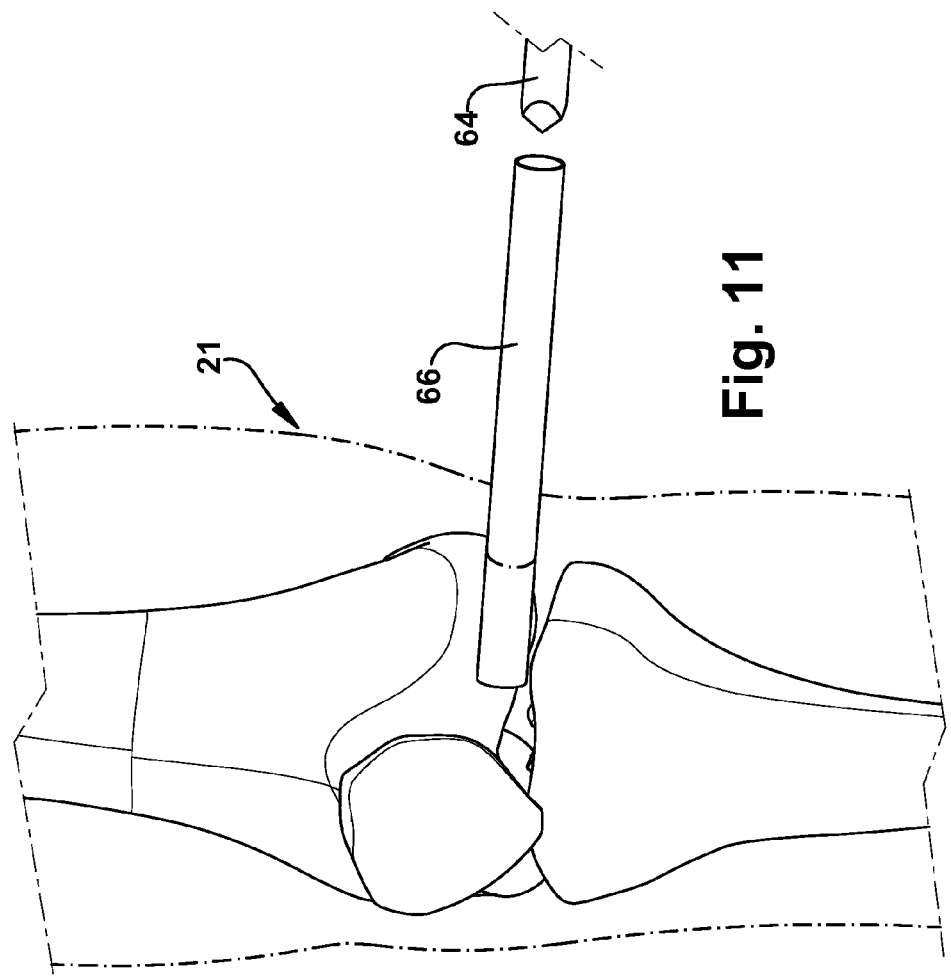
Figure 10:
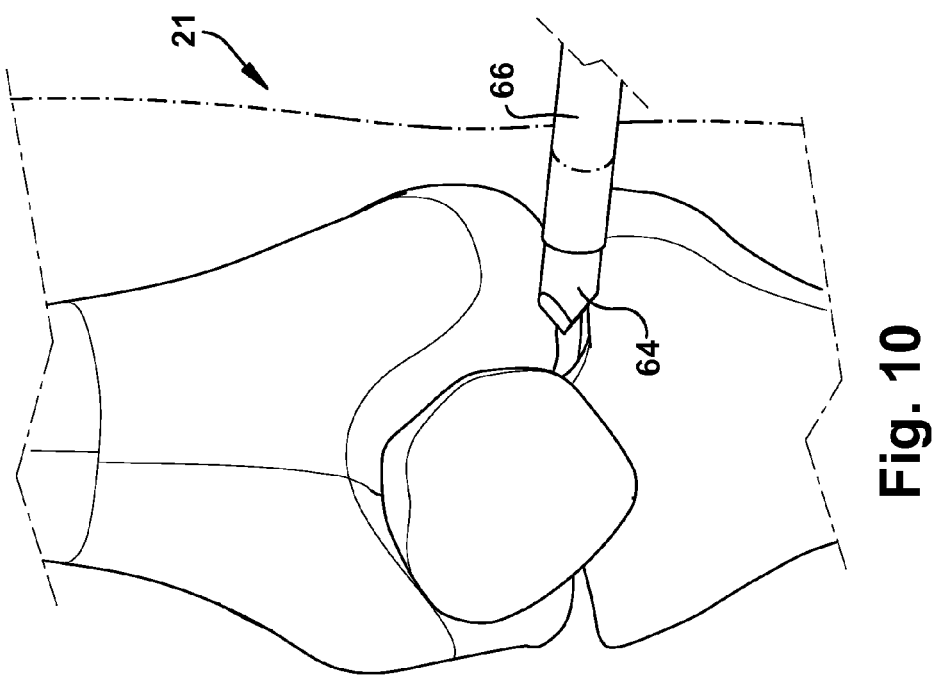
Figure 14:
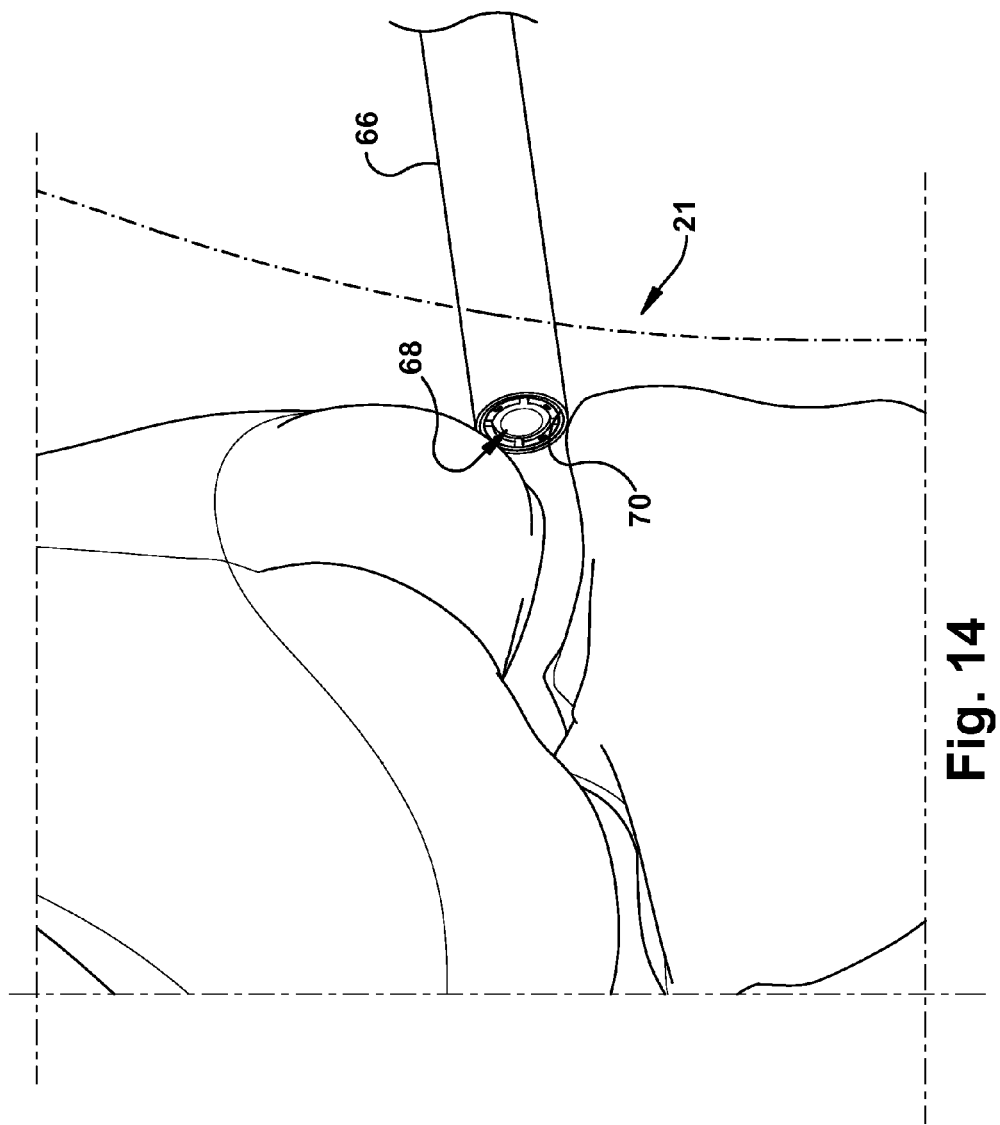
Figure 15:
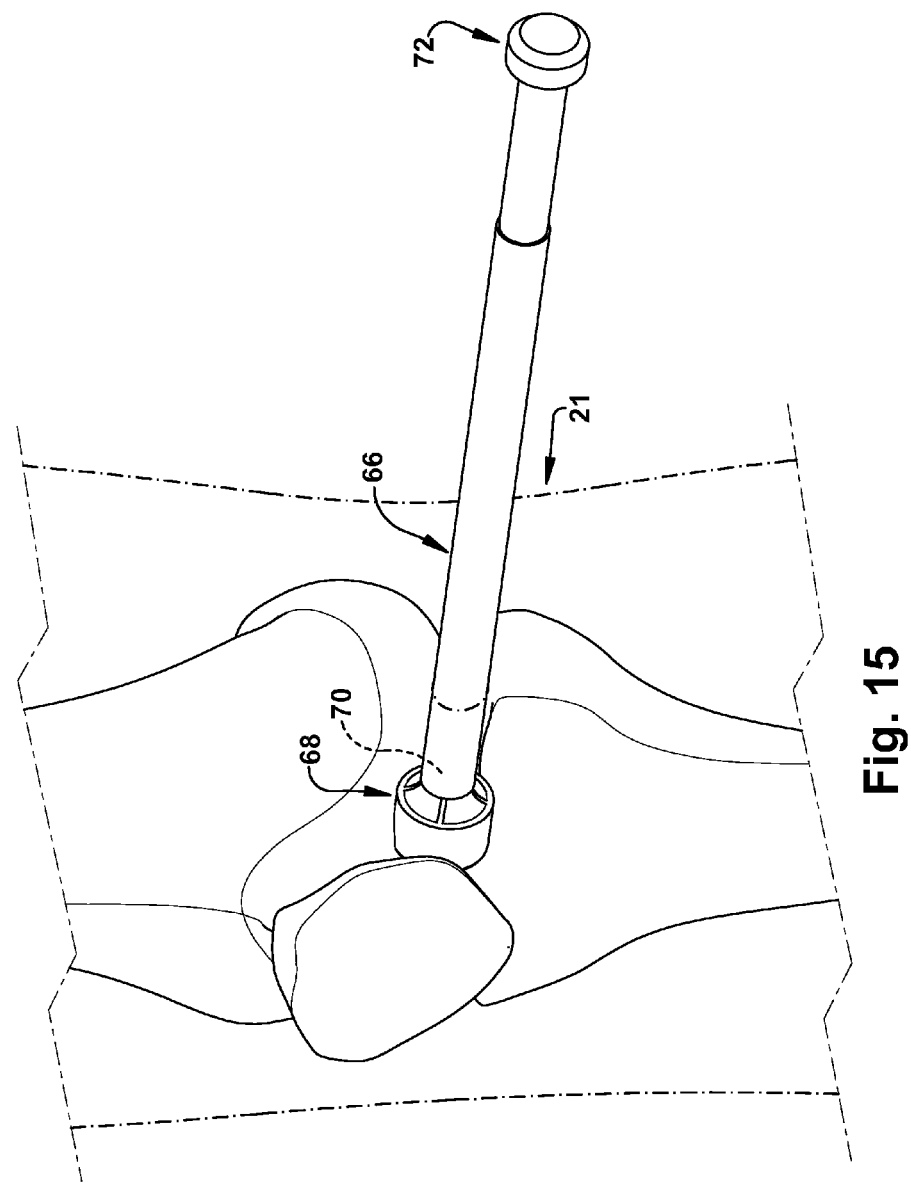
Figure 16:
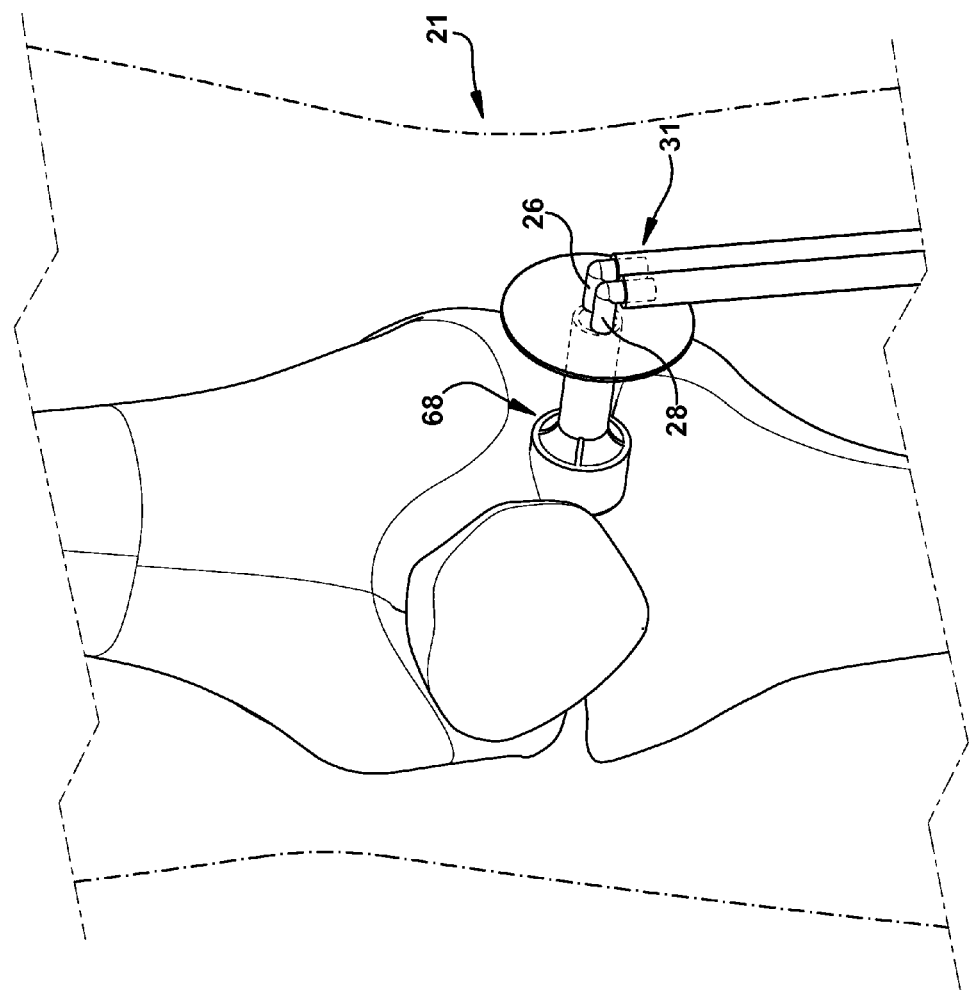

Although the above described systems and methods have been described with respect to open surgery, the present invention also provides systems and methods for treating an infection percutaneously. The following example steps are described with respect to percutaneously treating an infected virgin joint but could also be followed to treat an infected joint that has an existing implant. With reference to FIG. 10, a trocar 64 or similar device is inserted through an outer cannula 66 into the lateral side of an infected joint. Outer cannula 66 is left in the lateral side of the infected joint as depicted in FIG. 11. A cannula device 68, similar to cannula device 12 described above, is inserted into a loading cannula 70 as depicted in FIGS. 12A-12C. Loading cannula 70 housing cannula device 68 is inserted into outer cannula 66 as shown in FIGS. 13 and 14. Cannula device 68 is then deployed into the joint as depicted in FIG. 15. FIG. 15 illustrates a plunger 72 that urges cannula device 68 axially into the joint space but other instrumentation could be used as well. After cannula device 68 has been positioned in the joint space, an integrated pump and vacuum system 31 can be placed in fluid communication with the proximal end of the sponge of cannula device 68 as described above and as shown in FIG. 16 to irrigate the joint space.

Figure 17:
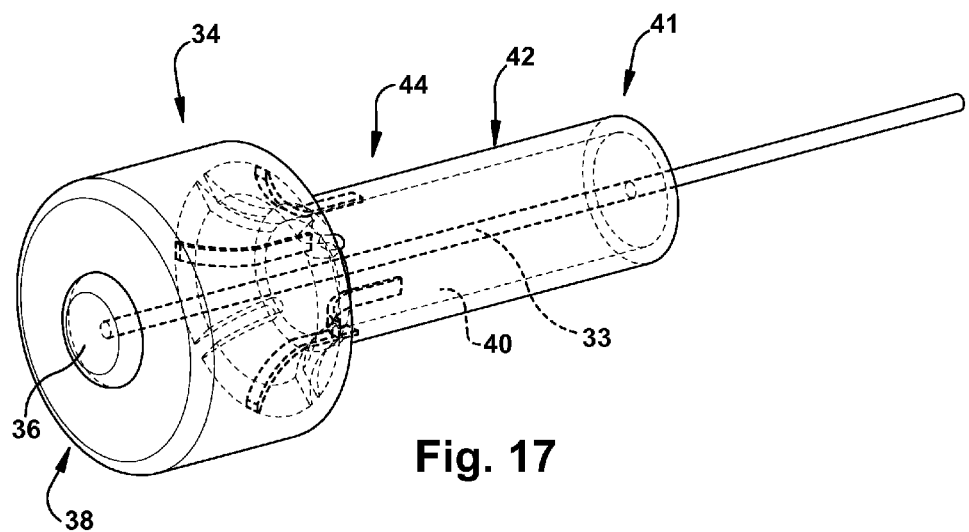
FIG. 17 is a side view of an embodiment of the present invention.

Once treatment is finished and/or a treatment cycle is completed, the cannula device or components thereof can be retrieved from the patient's body through the opening created in the patient's body to insert the cannula device. As such, the present invention provides other embodiments of a deployable infection treatment system that include features to retrieve the sponge and/or cannula body of a cannula device. For example, referring to FIG. 17, in an embodiment, the present invention provides a deployable infection treatment system 41 comprising a cannula device 44 similar to cannula device 12 described above and further including a retrieval cable 33 extending longitudinally through sponge 34 and attached to a fastener 36 at the distal end 38 of sponge 34. In the embodiment depicted in FIG. 17, the fastener is a metal cap on the exterior face of distal end 38 of sponge 34 but any suitable fastener that will securely fasten retrieval cable 33 to sponge 34 can be used. The metal cap in this embodiment has a diameter that matches the compressed diameter of sponge 34 when sponge 34 is in the lumen 40 of cannula body 42. The proximal portion of retrieval cable 33 outside of the patient's body can be bent or otherwise manipulated and secured out of the way until the treatment is complete. Once treatment is finished or a treatment cycle is completed, the retrieval cable can be pulled proximally and sponge 34 retracted into the cannula body 42 for removal from the patient's body. If another treatment cycle is necessary, a new sponge can be inserted into cannula body 42 and the joint space can be irrigated again.

Figure 18:
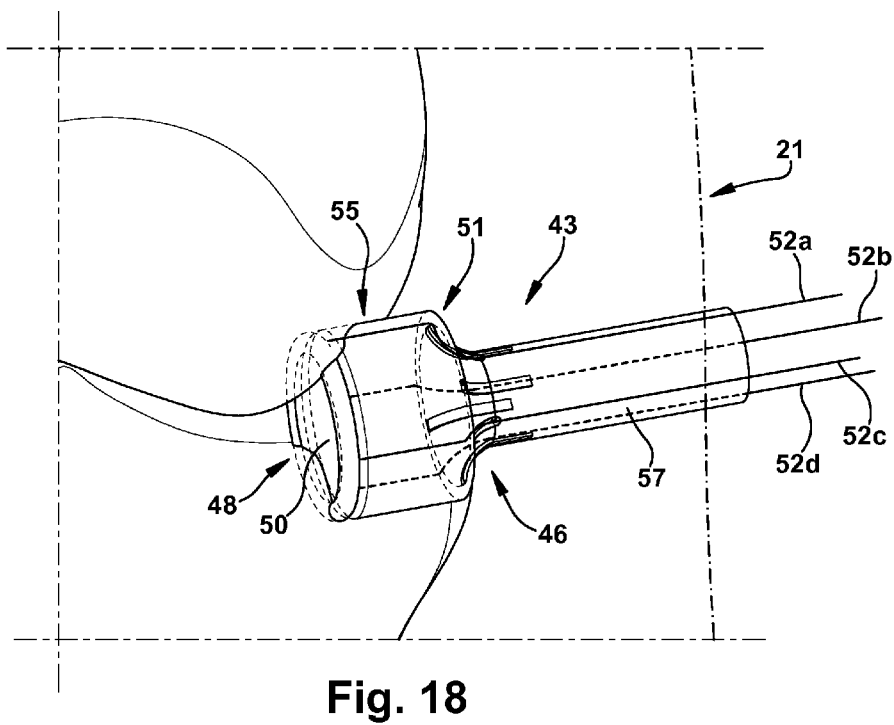
FIGS. 18-21 schematically depict a sequence of operation of an embodiment of the present invention in the example use environment of FIGS. 10-16.
Figure 19:
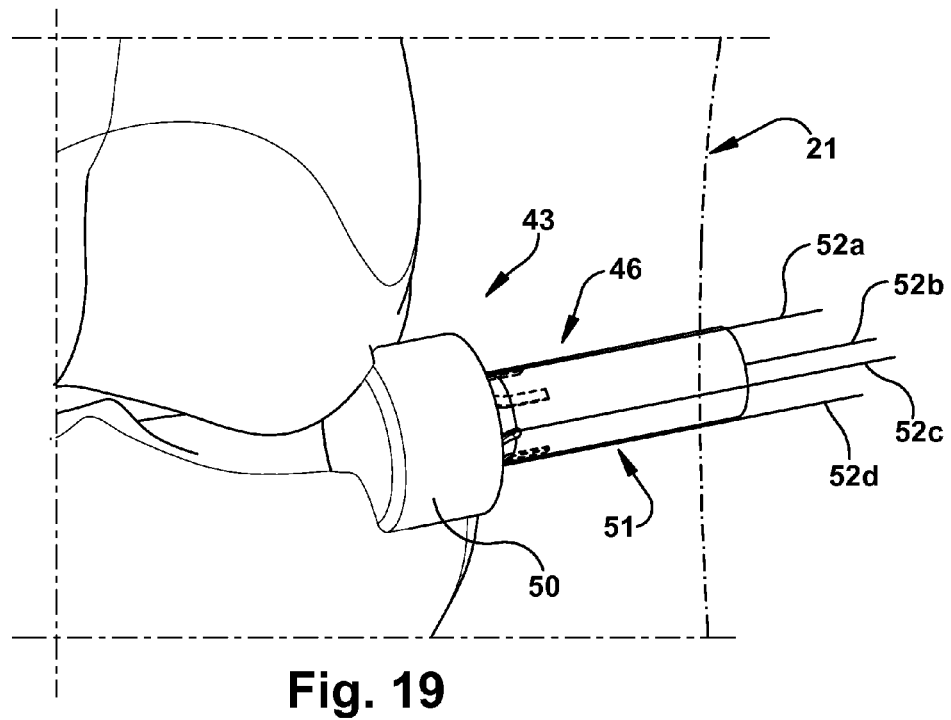
Figure 20:
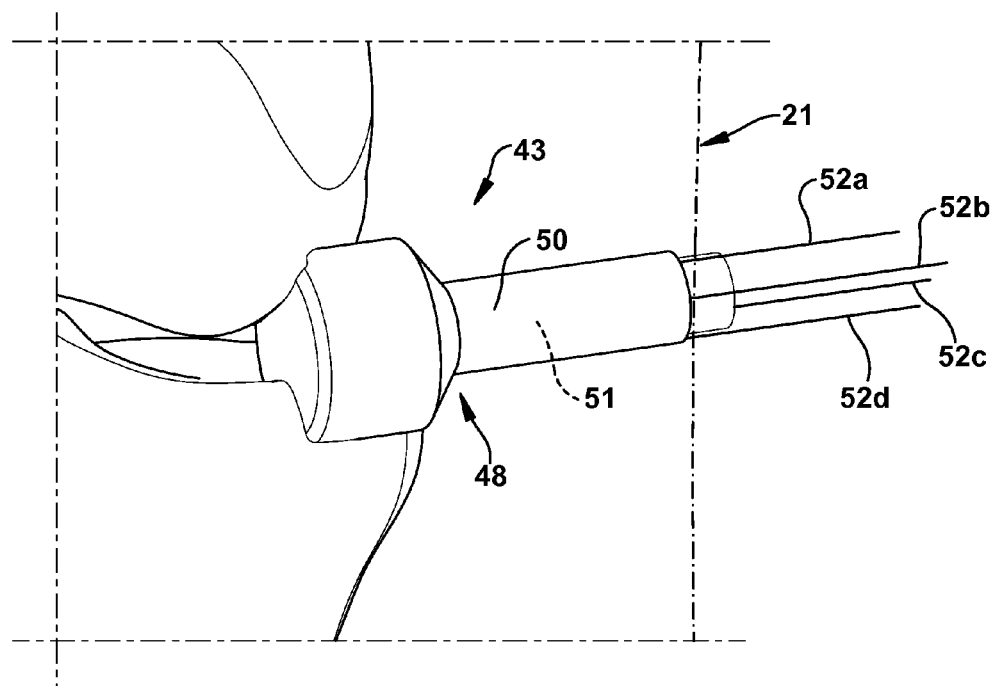
Figure 21:
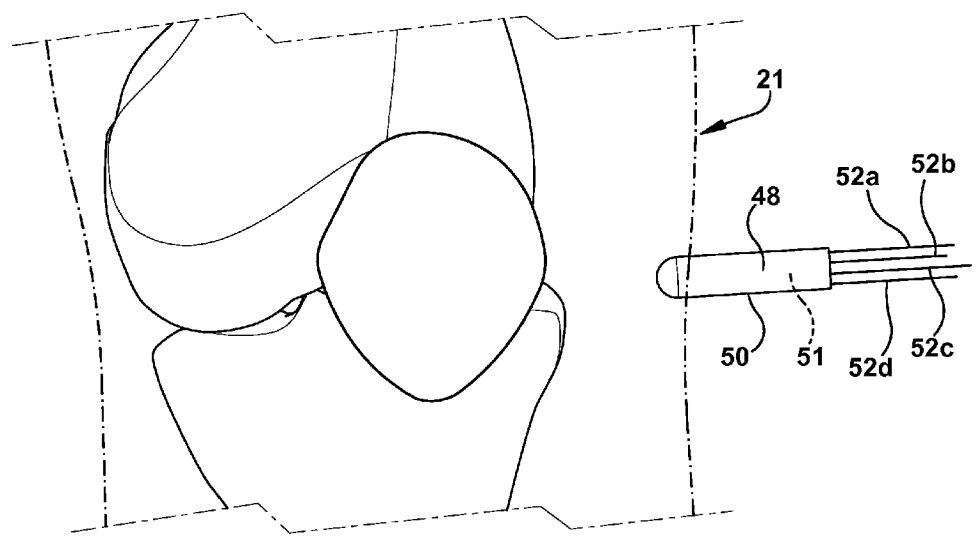

Referring to FIG. 18, in another embodiment, a deployable infection system 43 with a retrieval component comprises a cannula device 46 similar to cannula device 12 described above and further including a rollable sheath 48 disposed on the distal end 55 of sponge 51. Sheath 48 comprises a sleeve 50 and axially extending retrieval cords 52 attached to sleeve 50 and extending axially outside cannula body 57. Preferably, retrieval cords 52 are circumferentially spaced from one another as seen in FIG. 18. Once treatment is finished or a treatment cycle is completed, retrieval cords 52 can be pulled proximally thereby unrolling sheath 48 as seen in FIGS. 19 and 20 and covering sponge 51, similar to a condom usage. Sponge 51 can then be retracted from the patient's body as seen in FIG. 21. If another treatment cycle is necessary, a new sponge can be inserted into cannula body 57 and the joint space can be irrigated again.

Figure 22:
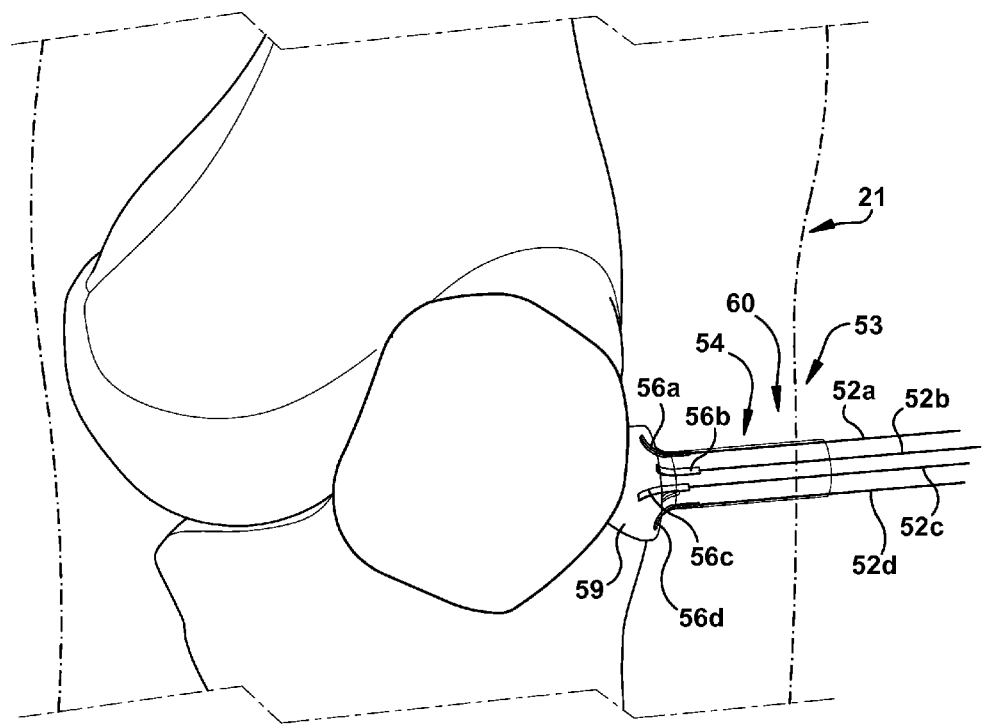
FIG. 22 schematically depicts an embodiment of the present invention in the example use environment of FIGS. 10-16.
Figure 23:
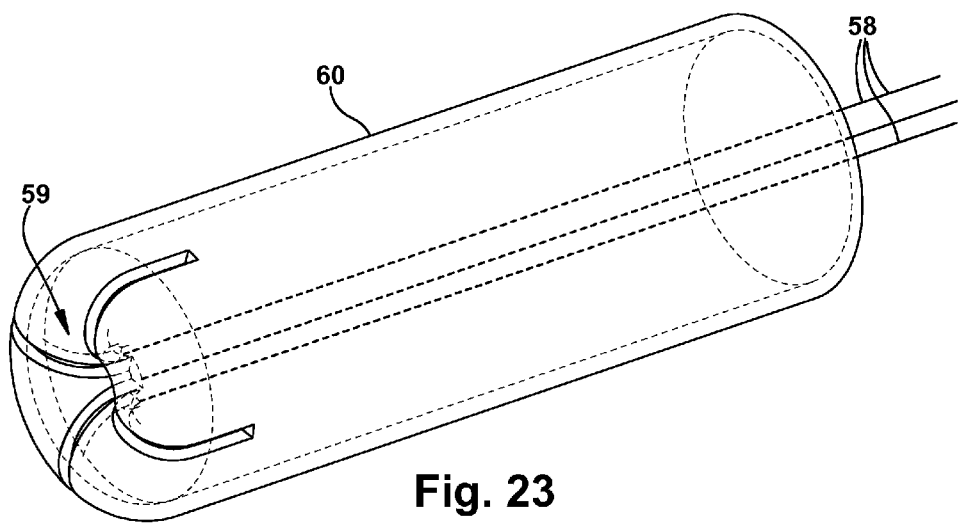
FIGS. 23-24 are side views of the embodiment of FIG. 22.
Figure 24:
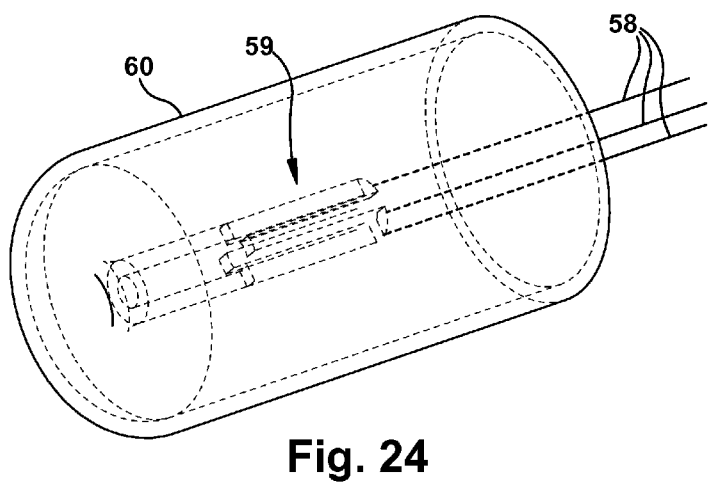

Referring to FIG. 22, in another embodiment, a deployable infection treatment system 53 with a retrieval component comprises a cannula device 54 similar to cannula device 12 described above and a plurality of elastic strips 56 disposed longitudinally about the flared distal end 59 of cannula body 60. The elastic strips can be fabricated from any suitable elastic material such as the shape memory material nitinol. System 53 further comprises a plurality of axially extending retrieval cables 58. Each one of the retrieval cables 58 is attached to a respective one of the elastic strips 56. For example, retrieval cable 58a is attached to elastic strip 58a. Preferably, strips 56 and their corresponding cables 58 are circumferentially spaced from one another as seen in FIG. 22. Once treatment is finished, retrieval cables 58 can be pulled proximally thereby inverting the flared distal end 59 of cannula body 60 as seen in FIGS. 23 and 24. As the retrieval cables 58 are continued to be pulled proximally, cannula body 60 continues to be inverted until it can be removed from the patient's body. As seen in FIG. 2, the flared distal end of the cannula body can define grooves 62 that aid in the flexibility of the distal end as it collapses onto itself during retrieval.

Figure 25:
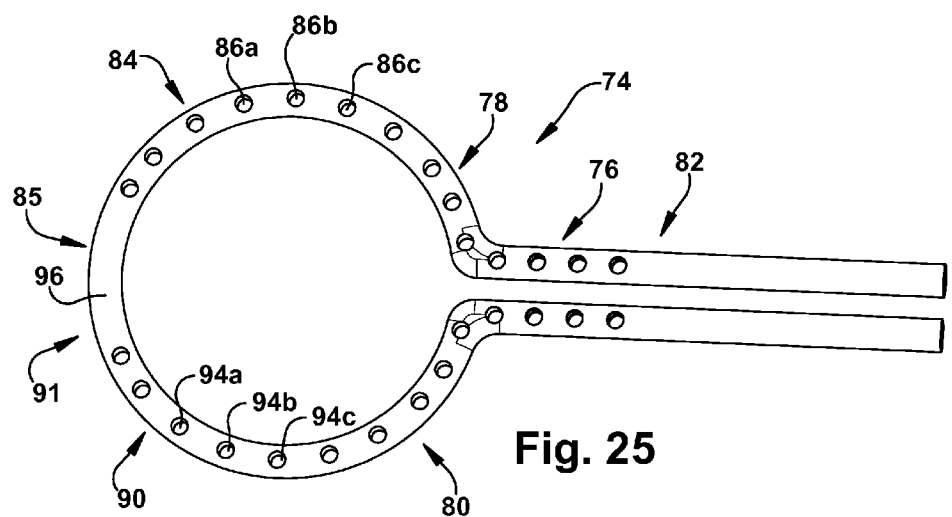
FIG. 25 is a top view of an embodiment of the present invention.

Referring to FIG. 25, in another embodiment, the present invention provides a deployable infection treatment system 74 comprising a cannula 76 having an outflow section 78 and an inflow section 80. Outflow section 78 has proximal portion 82 having an open proximal end 83 and a distal portion 84 having a closed distal end 85. An outflow channel 87 extends between proximal end 83 and distal end 85. Distal portion 84 comprises a plurality of outlets 86 in fluid communication with outflow channel 87. Inflow section 80 has a proximal portion 88 having an open proximal end 81 and a distal portion 90 having a closed distal end 91. An inflow channel 92 extends between proximal end 81 and distal end 91. Distal portion 90 of inflow section 80 comprises a plurality of inlets 94 in fluid communication with inflow channel 92. In a deployed configuration, the distal portions 84 and 90 of respective outflow section 78 and inflow section 80 are curved as seen in FIG. 24 to mutually form a loop-like shape. In certain embodiments, to ensure outflow channel 87 is separate from the inflow channel 92, cannula 76 comprises a solid midsection 96 disposed between outflow section 78 and inflow section 80. Solid midsection 96 essentially forms a wall to separate outflow and inflow channels 87 and 92, respectively.

Figure 27:
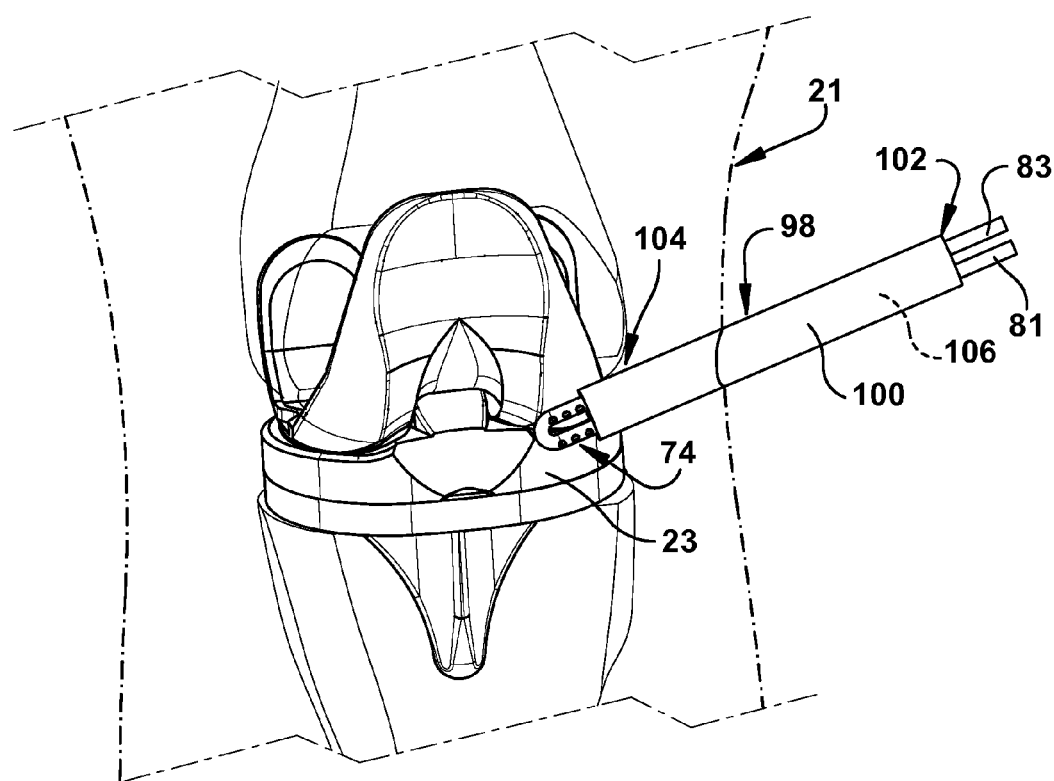
Figure 28:
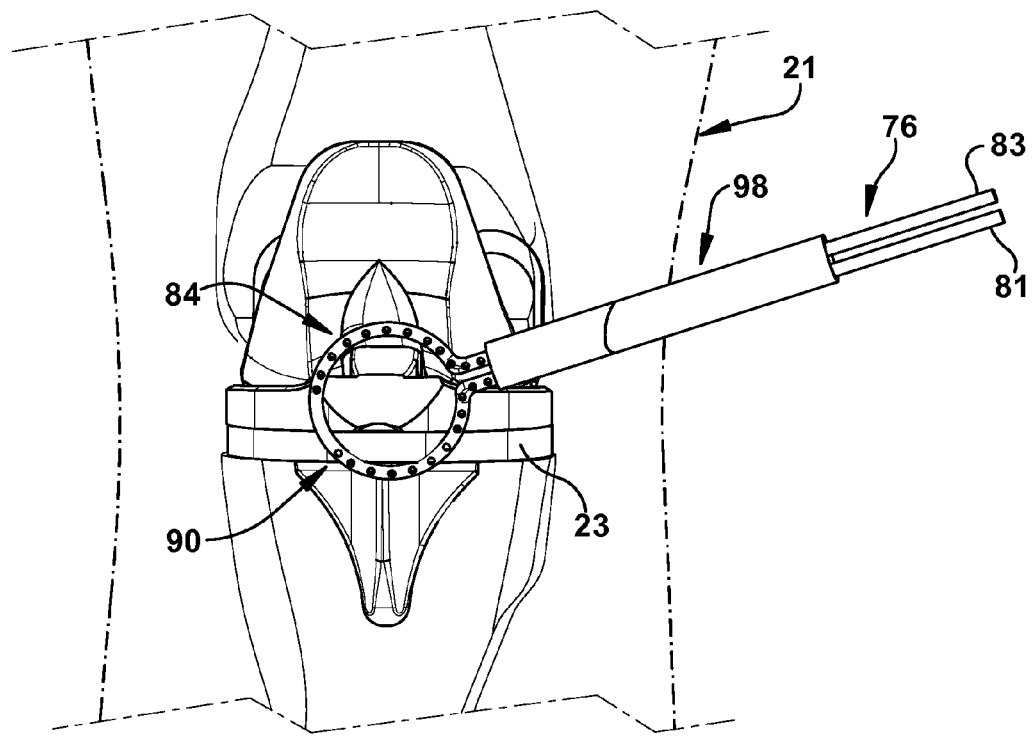

As seen in FIG. 27, in certain embodiments, deployable infection treatment system 74 comprises a sheath 98 comprising a sheath body 100 having a proximal end 102, a distal end 104, and a lumen 106 extending therebetween. When cannula 76 is in a deployed configuration, distal portions 84 and 90 of respective outflow section 78 and inflow section 80 are compressed within lumen 106 as seen in FIG. 27 and in a deployed configuration, the distal portions 84 and 90 assume the loop-like shape as seen in FIG. 28.

Figure 30:
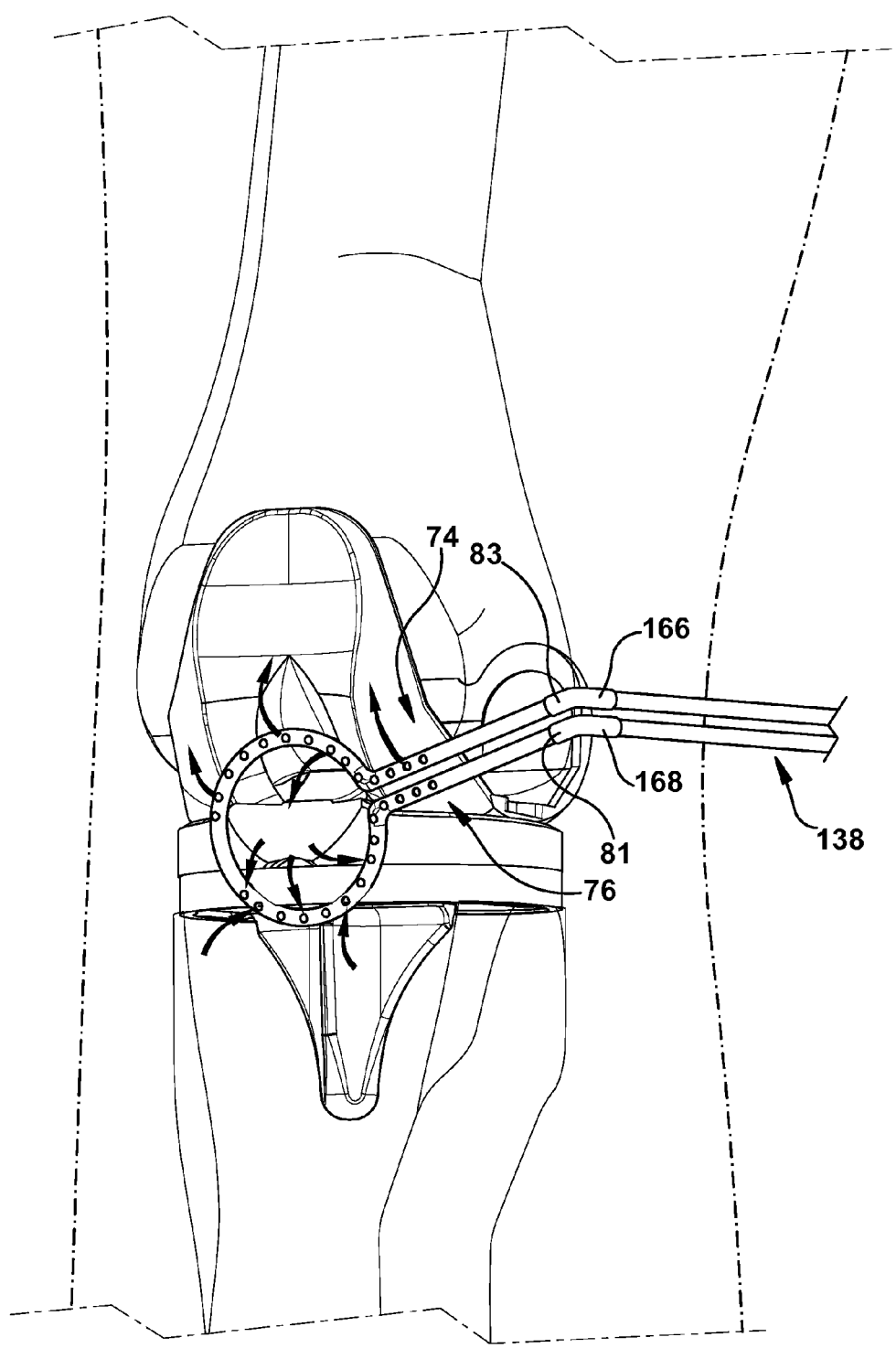

As with other embodiments, a deployable treatment system, such as system 74, comprises an integrated pump and vacuum device 138 as seen in FIG. 30. When cannula 76 is in a deployed configuration, cannula 76 is in fluid communication with a therapeutic fluid source. The pump controls delivery of the therapeutic fluid to proximal end 83 of outflow section 78 into outflow channel 87. The vacuum controls the extraction of therapeutic fluid and infectious material from proximal end 81 of inflow section 80 out of inflow channel 92. In certain embodiments, the integrated pump and vacuum device 138 comprises a first tube 166 having a distal end in fluid communication with proximal end 83 of outflow section 78 and a proximal end in fluid communication with a pump. The pump, in turn, is in fluid communication with the therapeutic fluid source. The integrated pump and vacuum device 138 further comprises a second tube 168 having a distal end in fluid communication with the proximal end 81 of inflow section 80 and a proximal end in fluid communication with a vacuum.

Figure 26:
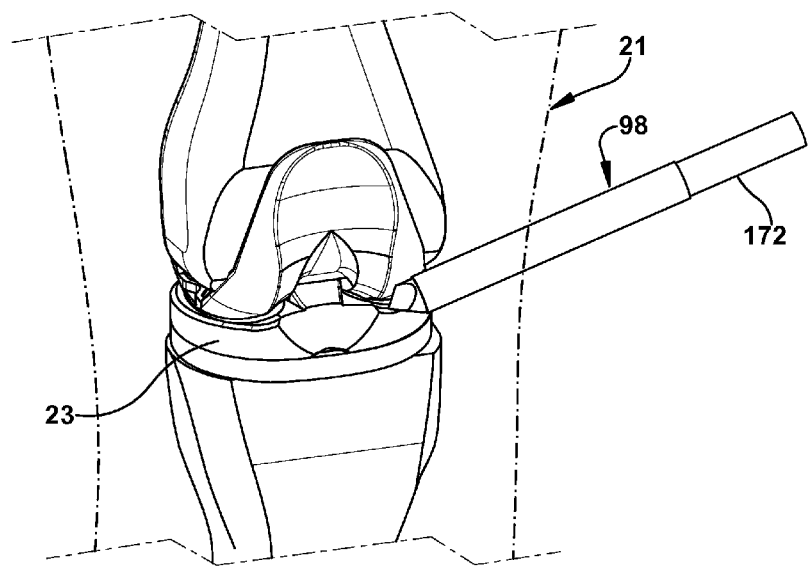
FIGS. 26-30 schematically depict the embodiment of FIG. 25 in the example use environment of FIGS. 3-9.
Figure 29:
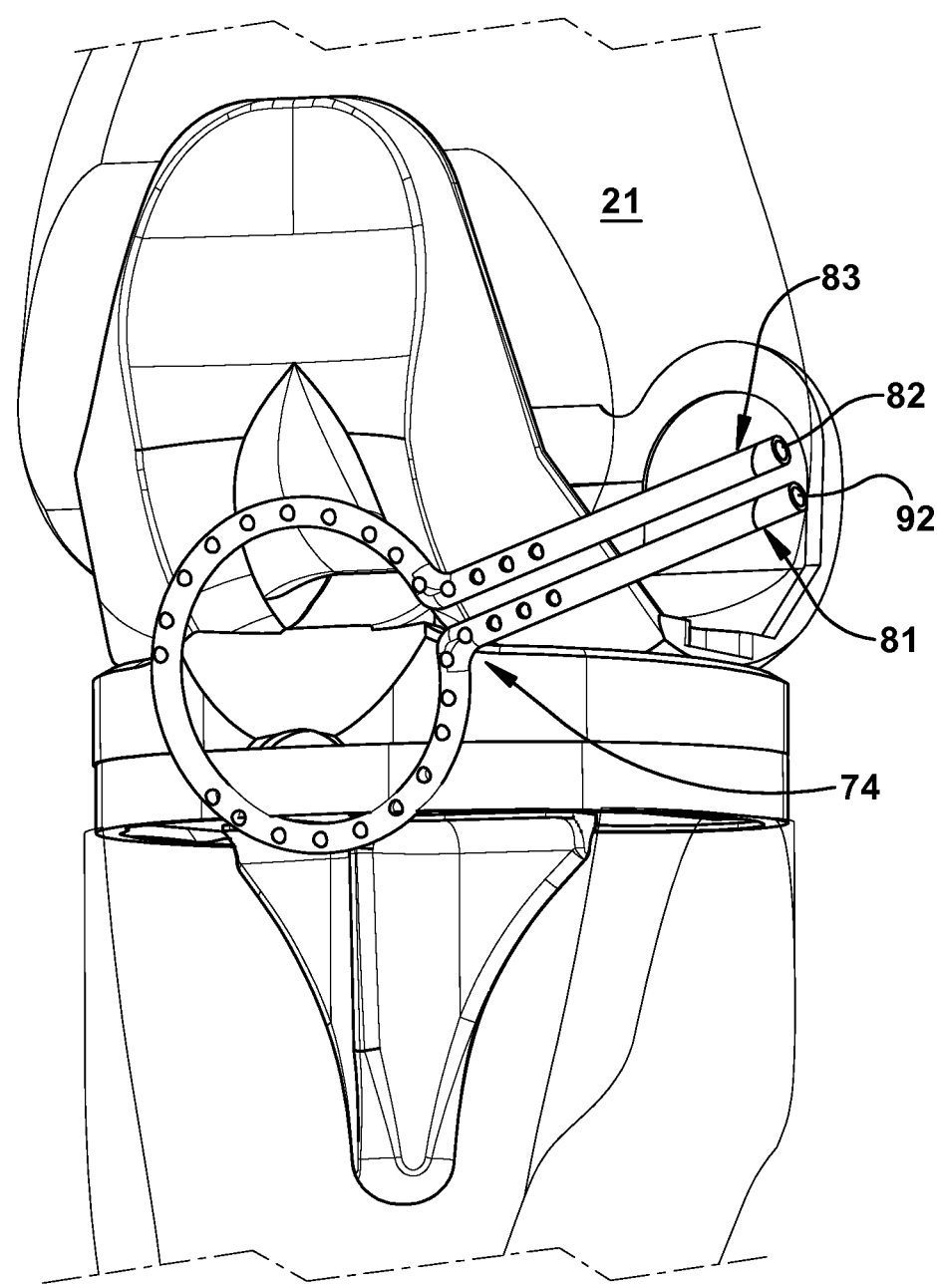

According to an example method of using a deployable treatment system, such as system 74, steps include inserting a trocar 172 or similar device into sheath 98 and piercing the lateral side of the patient's infected joint as seen in FIG. 26. Sheath 98 is left in place on the lateral side of the patient's knee and cannula 76 is inserted into sheath 98 as seen in FIG. 27. Cannula 76 is urged out of sheath 98 and distal portions 84 and 90 mutually assume a loop-like shape as seen in FIG. 28. Sheath 98 is removed and proximal ends 83 and 81 of respective inflow section 78 and outflow section 80 are exposed to the outside of the patient's body as seen in FIG. 29. A seen in FIG. 30, an integrated pump and vacuum device 138 is connected to cannula 76 and the joint is irrigated as described above.

Although FIG. 25 illustrates the distal portions 84 and 90 as mutually forming a loop-like shape in a deployed configuration, the distal portions of the cannula can have other shapes. For example, referring to FIG. 31, an embodiment of the present invention provides a cannula 108 having an outflow section 110 and an inflow section 112. Outflow section 110 has a proximal portion 114 having an open proximal end 116 and a distal portion 118 having an open distal end 120. An outflow channel 122 extends between proximal end 116 and distal end 120. Distal portion 118 comprises a plurality of outlets 124 in fluid communication with outflow channel 122. Inflow section 112 has a proximal portion 126 having an open proximal end 128 and a distal portion 130 having an open distal end 132. An inflow channel 134 extends between proximal end 116 and distal end 120. Distal portion 130 of inflow section 112 comprises a plurality of inlets 136 in fluid communication with inflow channel 134. In this embodiment, each of the distal portions 118 and 130 of outflow section 110 and inflow section 112 has a substantially rectangular cross-sectional shape as seen in FIGS. 31 and 32.

Figure 33:
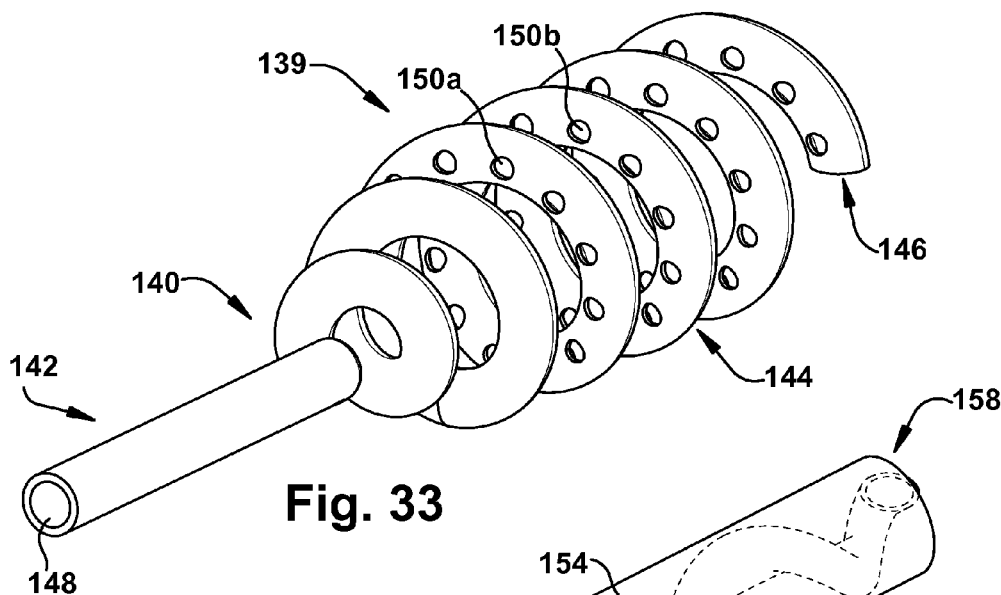
FIG. 33 is a perspective side view of an embodiment of the present invention.
Figure 34:
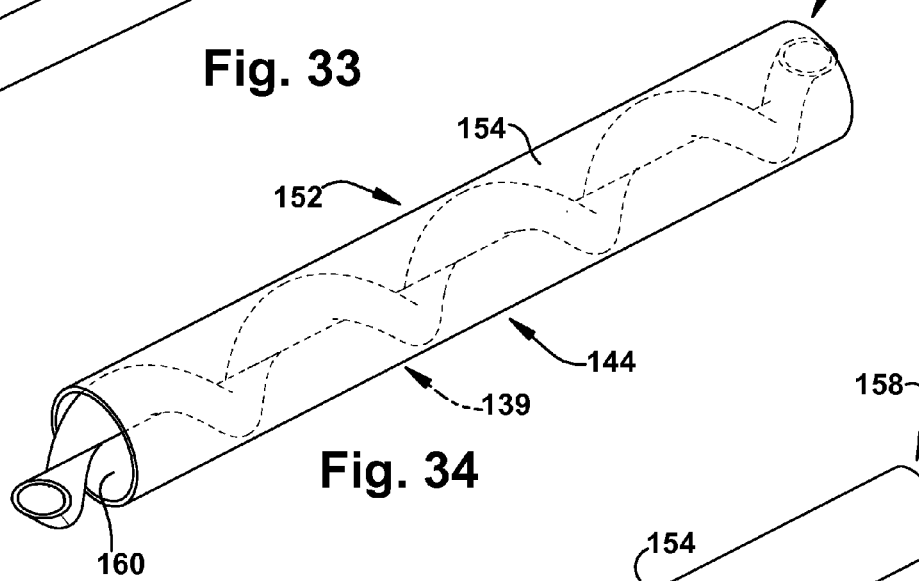
FIGS. 34-35 schematically depict a sequence of operation of the embodiment of FIG. 33.
Figure 35:
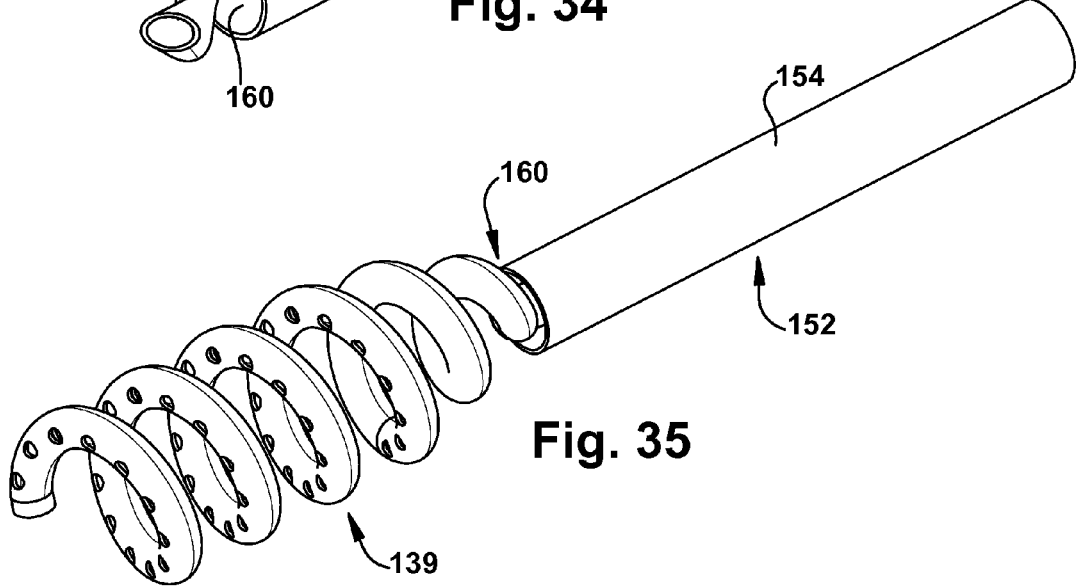

Referring to FIG. 33, in another embodiment, a cannula of a deployable infection treatment system has a spiral shape. In particular, cannula 139 comprises a proximal portion 140 with an open proximal end 142 and a helically shaped distal portion 144 with a closed distal end 146. A channel 148 extends between proximal end 142 and distal end 146. Distal portion 144 comprises a plurality of ports 150 that are in fluid communication with the channel 148. Referring to FIG. 34, the deployable infection treatment system can also include a sheath 152 comprising a sheath body 154 having a proximal end 156, a distal end 158, and a lumen 160 extending therebetween. When cannula 139 is in a non-deployed configuration, distal portion 144 is collapsed within lumen 160 as seen in FIG. 34 and in a deployed configuration, distal portion expands out from distal end 158 of sheath body 154 as seen in FIG. 35. In this embodiment, delivery of a therapeutic agent and suction occur through the same ports but at different times depending on the mode the integrated pump and vacuum device is in.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described system(s) and device(s) are merely illustrative; one of ordinary skill in the art could readily determine any number of tools, sequences of steps, or other means/options for placing the above-described apparatus, or components thereof, into positions substantially similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. Any of the components described herein could have a surface treatment (e.g., texturization, notching, etc.), material choice, and/or other characteristic chosen to provide the component with a desired interaction property (e.g., tissue ingrowth, eluting of a therapeutic material, etc.) with the surrounding tissue. A device or method incorporating any of these features should be understood to fall under the scope of the present invention as determined based upon the claims below and any equivalents thereof. Other aspects, objects, and advantages of the present invention can be obtained from a study of the drawings, the disclosure, and the appended claims.

Having described the invention, we claim:

1. A deployable infection treatment system comprising:
    a cannula device comprising:
        a cannula body having a proximal end, a flared distal end, and a lumen extending therebetween, the lumen having a longitudinal x-axis extending therethrough; and
        a selected one of a sponge or drain, the selected one of the sponge or drain having a distal end and a proximal end, wherein in a non-deployed configuration, the selected one of the sponge or drain is compressed within the cannula body's lumen and in a deployed configuration the distal end of the selected one of the sponge or drain expands out of the cannula body's lumen; and
    an integrated pump and vacuum device, wherein when the selected one of the sponge or drain is in a deployed configuration, the device is in fluid communication with a therapeutic fluid source, the pump controlling the delivery of the therapeutic fluid to the proximal end of the selected one of the sponge or drain, the vacuum controlling the extraction of the therapeutic fluid and infectious material from the proximal end of the selected one of the sponge or drain, the integrated pump and vacuum device including
        a first tube having a distal end in fluid communication with the proximal end of the selected one of the sponge or drain and a proximal end in fluid communication with the pump, the pump in fluid communication with the therapeutic fluid source, and
        a second tube having a distal end in fluid communication with the proximal end of the selected one of the sponge or drain and a proximal end in fluid communication with the vacuum.

2. The deployable infection treatment system of claim 1, wherein the distal end of the selected one of the sponge or drain has a diameter greater than the flared distal end of the cannula body in a deployed configuration of the selected one of the sponge or drain.

3. The deployable infection treatment system of claim 1, further comprising a retrieval cable extending through the selected one of the sponge or drain and attached to a fastener at the distal end of the selected one of the sponge or drain.

4. The deployable infection treatment system of claim 1, including a retrieval cable extending longitudinally through the selected one of the sponge or drain and attached to a fastener at the distal end of the selected one of the sponge or drain, and wherein the fastener is a cap.

5. The deployable infection treatment system of claim 4, wherein the cap is on an exterior face of the distal end of the selected one of the sponge or drain.

6. The deployable infection treatment system of claim 1, further comprising a rollable sheath disposed on the distal end of the sponge, the rollable sheath comprising a sleeve and axially extending retrieval cords attached to the sleeve.

7. The deployable infection treatment system of claim 1, further comprising a plurality of elastic bands disposed about the flared distal end of the cannula body.

8. The deployable infection treatment system of claim 1, wherein the plurality of elastic bands comprise nitinol.

9. The deployable infection treatment system of claim 7, further comprising a plurality of axially extending retrieval cables, each one of the plurality of retrieval cables attached to a respective one of the plurality of elastic bands.

10. A deployable infection treatment system comprising:
    a cannula device comprising:
        a cannula body having a proximal end, a flared distal end, and a lumen extending therebetween, the lumen having a longitudinal x-axis extending therethrough;
        a sponge having a distal end and a proximal end, wherein in a non-deployed configuration, the sponge is compressed within the cannula body's lumen and in a deployed configuration the distal end of the sponge expands out of the cannula body's lumen;
        a retrieval cable extending longitudinally through the sponge and attached to a fastener at the distal end of the sponge; and
    an integrated pump and vacuum device, wherein when the sponge is in a deployed configuration, the integrated device is in fluid communication with a therapeutic fluid source, the pump controlling the delivery of the therapeutic fluid to the proximal end of the sponge, the vacuum controlling the extraction of the therapeutic fluid and infectious material from the proximal end of the sponge, the integrated PUMP and vacuum device including
        a first tube having a distal end in fluid communication with the proximal end of the sponge and a proximal end in fluid communication with the pump, the PUMP in fluid communication with the therapeutic fluid source, and
        a second tube having a distal end in fluid communication with the proximal end of the sponge and a proximal end in fluid communication with the vacuum.

11. The deployable infection treatment system of claim 10, wherein the fastener comprises a cap on the exterior face of the distal end of the sponge.

12. A deployable infection treatment system comprising:
    a cannula device comprising:
        a cannula body having a proximal end, a flared distal end, and a lumen extending therebetween, the lumen having a longitudinal x-axis extending therethrough;
        a sponge having a distal end and a proximal end, wherein in a non-deployed configuration, the sponge is compressed within the cannula body's lumen and in a deployed configuration the distal end of the sponge expands out of the cannula body's lumen; and
        a rollable sheath disposed on the distal end of the sponge, the rollable sheath comprising a sleeve and axially extending retrieval cords attached to the sleeve and axially extending through the cannula body.

13. The deployable infection treatment system of claim 12, further comprising a plurality of elastic strips axially disposed about the flared distal end of the cannula body.

14. The deployable infection treatment system of claim 13, wherein the plurality of elastic strips comprise nitinol.

15. The deployable infection treatment system of claim 12, further comprising a plurality of axially extending retrieval cables, each one of the plurality of retrieval cables attached to a respective one of the plurality of elastic strips.

* * * * *

UNITED STATES PATENT AND TRADEMARK OFFICE
CERTIFICATE OF CORRECTION

PATENT NO. : 9,623,178 B2
APPLICATION NO. : 14/151025
DATED : April 18, 2017
INVENTOR(S) : Viktor E. Krebs et al.

Page 1 of 1

It is certified that error appears in the above-identified patent and that said Letters Patent is hereby corrected as shown below:

In the Claims
Column 10, Line 25 reads "PUMP" should read --pump--
Column 10, Line 29 reads "PUMP" should read --pump--

Signed and Sealed this
Thirtieth Day of May, 2017

Michelle K. Lee
*Director of the United States Patent and Trademark Office*